(12) United States Patent
O'Reilly et al.

(10) Patent No.: US 10,342,864 B2
(45) Date of Patent: Jul. 9, 2019

(54) METHODS OF TREATING CMV RETINITIS BY T CELL THERAPY

(71) Applicants: Memorial Sloan Kettering Cancer Center, New York, NY (US); Cornell University, Ithaca, NY (US)

(72) Inventors: Richard John O'Reilly, Roxbury, CT (US); Susan Elizabeth Prockop, New York, NY (US); Ekaterina Doubrovina, Bronx, NY (US); Guenther Koehne, New York, NY (US); Aisha Nasreen Hasan, New York, NY (US); Szilard Kiss, New York, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 0 days.

(21) Appl. No.: 15/191,773

(22) Filed: Jun. 24, 2016

(65) Prior Publication Data

US 2017/0128565 A1    May 11, 2017

Related U.S. Application Data

(60) Provisional application No. 62/191,304, filed on Jul. 10, 2015, provisional application No. 62/185,558, filed on Jun. 26, 2015.

(51) Int. Cl.

| | | |
|---|---|---|
| *C12Q 1/70* | (2006.01) | |
| *A61K 35/17* | (2015.01) | |
| *A61K 39/00* | (2006.01) | |
| *A61K 39/12* | (2006.01) | |
| *A61K 45/06* | (2006.01) | |
| *A61K 39/245* | (2006.01) | |

(52) U.S. Cl.
CPC ............ *A61K 39/245* (2013.01); *A61K 35/17* (2013.01); *A61K 39/12* (2013.01); *A61K 45/06* (2013.01); *C12Q 1/705* (2013.01); *A61K 2039/5158* (2013.01); *C12N 2710/16134* (2013.01)

(58) Field of Classification Search
CPC .................... A61K 35/17; A61K 39/12; A61K 2039/5158; A61K 39/245; A61K 2039/572; A61K 2039/57; A61K 39/00; A61K 38/00; A61K 2035/124; C12N 5/0636; C12N 7/00; C12N 2710/16134; C12N 5/0638; C12N 2506/11; C12N 2710/16171; C07K 14/005; C07K 16/085
See application file for complete search history.

(56) References Cited

U.S. PATENT DOCUMENTS

| | | | |
|---|---|---|---|
| 6,074,645 A | 6/2000 | Diamond et al. | |
| 6,544,521 B2 | 4/2003 | Diamond | |
| 7,041,442 B1 | 5/2006 | Kern et al. | |
| 7,163,685 B2 | 1/2007 | Diamond et al. | |
| 7,718,196 B2 | 5/2010 | Fowler et al. | |
| 8,425,898 B2 | 4/2013 | Sampson et al. | |
| 8,722,048 B2 | 5/2014 | Stauss et al. | |
| 9,011,835 B2 | 4/2015 | Sampson et al. | |
| 2004/0265325 A1* | 12/2004 | Diamond ............. | A61K 39/245 424/186.1 |
| 2005/0221381 A1 | 10/2005 | Klade et al. | |
| 2010/0151492 A1 | 6/2010 | Ahmed et al. | |
| 2011/0182870 A1 | 7/2011 | Leen et al. | |
| 2014/0303092 A1* | 10/2014 | Painter ................. | A61K 31/675 514/20.5 |
| 2015/0044258 A1* | 2/2015 | Knaus ................... | A61K 39/12 424/230.1 |
| 2016/0375060 A1* | 12/2016 | O'Reilly .............. | A61K 9/0019 424/93.71 |

FOREIGN PATENT DOCUMENTS

EP      1 023 319 B1    9/2004

OTHER PUBLICATIONS

Amarnath S, Fowler DH. Harnessing Autophagy for Adoptive T Cell Therapy. Immunotherapy. 2012;4(1):1-4.*
Humar A, Snydman D; AST Infectious Diseases Community of Practice. Cytomegalovirus in solid organ transplant recipients. Am J Transplant. Dec. 2009;9 Suppl 4:S78-86.*
Sylwester AW, Mitchell BL, Edgar JB, Taormina C, Pelte C, Ruchti F, Sleath PR, Grabstein KH, Hosken NA, Kern F, Nelson JA, Picker LJ. Broadly targeted human cytomegalovirus-specific CD4+ and CD8+ T cells dominate the memory compartments of exposed subjects. J Exp Med. Sep. 5, 2005;202(5):673-85.*
Giest S, McWhinnie A, Lefranc MP, Little AM, Grace S, Mackinnon S, Madrigal JA, Travers PJ. Cytomegalovirus-specific CD8+ T cells targeting different peptide/HLA combinations demonstrate varying T-cell receptor diversity. Immunology. Jan. 2012;135(1):27-39.*
Malouli D, Hansen SG, Nakayasu ES, Marshall EE, Hughes CM, Ventura AB, Gilbride RM, Lewis MS, Xu G, Kreklywich C, Whizin N, Fischer M, et. al. Cytomegalovirus pp65 limits dissemination but is dispensable for persistence. J Clin Invest. May 2014;124(5): 1928-44. Epub Apr. 1, 2014.*
International Search Report, Information on Search Strategy, and Written Opinion of the International Searching Authority, for International Patent Application No. PCT/US2016/038530, dated Dec. 13, 2016, 20 pages.
Schmitt et al., Mar. 2011, "Adoptive transfer and selective reconstitution of streptamer-selected cytomegalovirus-specific CD8+ T cells leads to virus clearance in patients after allogeneic peripheral blood stem cell transplantation," Transfusion, 51(3):591-599 (Published online Dec. 6, 2010).
Micklethwaite et al., Jun. 2007, "Ex vivo expansion and prophylactic infusion of CMV-pp65 peptide-specific cytotoxic T-lymphocytes following allogeneic hematopoietic stem cell transplantation," Biology of Blood and Marrow Transplantation, 13(6):707-714 (Published Apr. 6, 2007).

(Continued)

*Primary Examiner* — Rachel B Gill
(74) *Attorney, Agent, or Firm* — Jones Day

(57) ABSTRACT

Methods of treating CMV (cytomegalovirus) retinitis in a human patient in need thereof, comprising administering to the human patient a population of allogeneic T cells comprising CMV-specific T cells, wherein the human patient is infected with human immunodeficiency virus (HIV) or has been the recipient of a solid organ transplant.

54 Claims, 5 Drawing Sheets

(56) References Cited

OTHER PUBLICATIONS

Cobbold et al., Aug. 2005, "Adoptive transfer of cytomegalovirus-specific CTL to stem cell transplant patients after selection by HLA-peptide tetramers," The Journal of Experimental Medicine, 202(3):379-386.
Peggs et al., Oct. 2003, "Adoptive cellular therapy for early cytomegalovirus infection after allogeneic stem-cell transplantation with virus-specific T-cell lines," Lancet, 362(9393):1375-1377.
Invitation to Pay Additional Fees and, Where Applicable, Protest Fee, and Communication Relating to the Results of the Partial International Search of International Patent Application No. PCT/US2016/038530, International Searching Authority, dated Oct. 13, 2016, 10 pages.
Artherron et al.,Nov. 1992, "T cell depletion increases susceptibility to murine cytomegolovirus retinitis," Investigative Ophthalmology & Visual Science, 33(12):3353-3360.
Bao et al., Apr. 2012, "Adoptive immunotherapy with CMV specific cytotoxic T lymphocytes for stem cell transplant patients with refractory CMV infections," Journal of Immunotherapy, 35(3):293-298.
Barker and Billingham, 1977, "Immunologically privileged sites," Advances in Immunology, 25:1-54.
Bidanset et al., Jul. 2001, "Replication of human cytomegalovirus in severe combined immunodeficient mice implanted with human retinal tissue," The Journal of Infectious Diseases, 184:192-195 (Published online Jun. 8, 2001).
Bigger et al., Oct. 1999, "Protection against murine cytomegalovirus retinitis by adoptive transfer of virus-specific CD8+ T cells," Investigative Ophthalmology & Visual Science, 40(11):2608-2613.
Brown et al., Jun. 1995, "Dramatic interstrain differences in the replication of human cytomegalovirus in SCID-hu mice," The Journal of Infectious Diseases, 171(6):1599-1603.
Chee et al., 1990, "Analysis of the protein-coding content of the sequence of human cytomegalovirus strain AD169," Current Topics in Microbiology and Immunology, 154:125-169.
Conboy et al., Sep. 1987, "Early clinical manifestations and intellectual outcome in children with symptomatic congenital cytomegalovirus infection," The Journal of Pediatrics, 111(3):343-348.
Cortivo et al., Nov. 2012, "Anti CMV and/or anti adenovirus IFN-g-positive CD4+ CD8+ T lymphocytes for treatment of viral infections after allogeneic HSC transplantation: first results," Blood, 120(21):1906.
Crippa et al., Jan. 2001, "Virological, clinical, and ophthalmologic features of cytomegalovirus retinitis after hematopoietic stem cell transplantation," Clinical Infectious Diseases, 32(2):214-219 (Published online Jan. 15, 2001).
Crough and Khanna, Jan. 2009, "Immunobiology of human cytomegalovirus: from bench to bedside," Clinical Microbiology Reviews, 22(1):76-98.
Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).
Egbert et al., Nov. 1980, "Cytomegalovirus retinitis in immunosuppressed hosts. II. Ocular manifestations," Annals of Internal Medicine, 93(5): 664-670.
Egli et al., Feb. 2008, "'Cytomegalovirus-associated chorioretinitis after liver transplantation: case report and review of the literature," Transplant Infectious Disease, 10(1):27-43 (Published online Dec. 17, 2007).
Eid et al., Feb. 2008, "Clinical features and outcomes of cytomegalovirus retinitis after transplantation," Transplant Infectious Disease 10(1):13-18 (Published online May 19, 2007).
Einsele et al., Jun. 2002, "Infusion of cytomegalovirus (CMV)-specific T cells for the treatment of CMV infection not responding to antiviral chemotherapy," Blood, 99(11):3916-3922.
Eiz-Vesper et al., Jan. 2013, "Adoptive T-cell immunotherapy from third-party donors: characterization of donors and set up of a T-cell donor registry," Frontiers in Immunology, 3:410.
Feuchtinger et al., Nov. 2010, "Adoptive transfer of pp65-specific T cells for the treatment of chemorefractory cytomegalovirus disease or reactivation after haploidentical and matched unrelated stem cell transplantation," Blood, 116(20):4360-4367 (Published online Jul. 12, 2010).
Fishman, Dec. 2007, "Infection in solid-organ transplant recipients," The New England Journal of Medicine, 357(25):2601-2614.
"Form S-1 Registration Statement," filed with the United States Securities and Exchange Commission by Atara Biotherapeutics, Inc., dated Jun. 29, 2015, 203 pages.
Fowler et al., Mar. 1992, "The outcome of congenital cytomegalovirus infection in relation to maternal antibody status," The New England Journal of Medicine 326:663-667.
Gabrielian et al., Dec. 1994, "Effect of TGF-beta on interferon-gamma-induced HLA-DR expression in human retinal pigment epithelial cells," Investigative Ophthalmology & Visual Science, 35(13):4253-4259.
Gahn et al., Jan. 2002, "Immunotherapy to reconstitute immunity to DNA viruses," Seminars in Hematology, 39(1):41-47.
Griffith et al., Nov. 1995, "Fas ligand-induced apoptosis as a mechanism of immune privilege," Science, 270(5239):1189-1192.
Gupta et al., "Treatment of cytomegalovirus (CMV) retinitis with third party donor-derived CMV-specific cytotoxic T-lymphocytes," meeting abstract for ASRS 33rd Annual Meeting held Jul. 11-14, 2015, Vienna, Austria, released on Jul. 1, 2015, 2 pages.
Gupta et al., Jan. 2015, "Treatment of cytomegalovirus retinitis with cytomegalovirus-specific T-lymphocyte infusion," Ophthalmic Surgery, Lasers & Imaging Retina, 46(1):80-82.
Hakki et al., Oct. 2003, "Immune reconstitution to cytomegalovirus after allogeneic hematopoietic stem cell transplantation: impact of host factors, drug therapy, and subclinical reactivation," Blood, 102:3060-3067 (Published online Jul. 3, 2003).
Hammond et al., Apr. 2013, "Cytomegalovirus disease in lung transplantation: impact of recipient seropositivity and duration of antiviral prophylaxis," Transplant Infectious Disease, 15(2):163-170 (Published online Dec. 12, 2012).
Harvala et al., May 2013, "High risk of cytomegalovirus infection following solid organ transplantation despite prophylactic therapy," Journal of Medical Virology, 85(5):893-898.
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).
Hasan et al., Nov. 2013, "Generation and characterization of a third party GMP grade bank of CMV specific T-cells for adoptive immunotherapy of CMV infections in recipients of HSCT from cord blood or seronegative donors," Blood, 122(21):2021.
Hasan et al., Dec. 2014, "Banked, GMP grade third party T-cell lines specific for CMVpp65 epitopes presented by certain prevalent HLA alleles more consistently clear CMV infections in a genetically heterogeneous population of HSCT recipients," Blood, 124(21):309.
Hasan et al., Feb. 2014, "Generation and characterization of a third party GMP grade bank of CMV specific T-cells for adoptive immunotherapy of CMV infections in recipients of HSCT from cord blood or seronegative donors," Biology of Blood and Marrow Transplantation, 20(2):S131-S132.
Hasan, "Banked, GMP grade third party T-cell lines specific for CMVpp65 epitopes presented by certain prevalent HLA alleles more consistently clear CMV infections in a genetically heterogeneous population of HSCT recipients," slide presentation on Dec. 8, 2014 at the 56th ASH Annual Meeting held Dec. 6-9, 2014, San Francisco, California, United States, 22 pages.
Holbrook et al., Jan. 2003, "Visual loss in patients with cytomegalovirus retinitis and acquired immunodeficiency syndrome before widespread availability of highly active antiretroviral therapy," Archives of Ophthalmology, 121(1):99-107.
Holmes-Liew et al., Mar. 2015, "Adoptive T-cell immunotherapy for ganciclovir-resistant CMV disease after lung transplantation," Clinical & Translational Immunology, 4(3):e35.

(56) References Cited

OTHER PUBLICATIONS

Hoover et al., Jul. 1996, "Occurrence of cytomegalovirus retinitis after human immunodeficiency virus immunosuppression," Archives of Ophthalmology, 114(7): 821-827.

Jabs et al., Jul. 1989, "Ocular manifestations of acquired immune deficiency syndrome," Ophthalmology, 96(7):1092-1099.

Jabs et al., Nov. 2010, "Course of cytomegalovirus retinitis in the era of highly active antiretroviral therapy: five-year outcomes," Ophthalmology, 117(11):2152-2161 e1-2 (Published online Jul. 29, 2010).

Jabs et al., Jun. 2013, "Comparison of treatment regimens for cytomegalovirus retinitis in patients with AIDS in the era of highly active antiretroviral therapy," Ophthalmology, 120(6):1262-1270 (Published online Feb. 16, 2013).

Jabs et al., Jul. 2015, "Long-term outcomes of cytomegalovirus retinitis in the era of modern antiretroviral therapy: results from a United States cohort," Ophthalmology, 122(7):1452-1463 (Published online Apr. 17, 2015).

Jacobson and Mills, Apr. 1988, "Serious cytomegalovirus disease in the acquired immunodeficiency syndrome (AIDS). Clinical findings, diagnosis, and treatment," Annals of Internal Medicine, 108(4):585-594.

Jacobson et al., Jan. 2000, "Natural history and outcome of new AIDS-related cytomegalovirus retinitis diagnosed in the era of highly active antiretroviral therapy," Clinical Infectious Diseases, 30(1):231-233.

Kawakami et al., Oct. 2005, "A case of immune recovery vitritis induced by donor leukocyte infusion for the treatment of cytomegalovirus retinitis," European Journal of Haematology, 75(4):352-354.

Kern, Sep. 2006, "Pivotal role of animal models in the development of new therapies for cytomegalovirus infections," Antiviral Research, 71(2-3):164-171 (Published online Jun. 19, 2006).

Khare and Sharland, Aug. 2011, "Cytomegalovirus treatment options in immunocompromised patients," Expert Opinion on Pharmacotherapy, 2(8):1247-1257.

Kiss et al., "Treatment of cytomegalovirus (CMV) retinitis with systemic infusion of third party donor-derived CMV-specific cytotoxic T-lymphocytes," meeting abstract for the Retina Society 48th Annual Scientific Meeting held Oct. 7-11, 2015, Paris, France, released Oct. 7, 2015, 1 pages.

Koehne et al., Sep. 2015, "Immunotherapy with donor T cells sensitized with overlapping pentadecapeptides for treatment of persistent cytomegalovirus infection or viremia," Biology of Blood and Marrow Transplantation, 21(9):1663-1678 (Published online May 29, 2015).

Kumar et al., May 2009, "Cell-mediated immunity to predict cytomegalovirus disease in high-risk solid organ transplant recipients," The American Journal of Transplantation, 9(5):1214-1222.

Lam and Khan, May 1997, "Cytomegalovirus in transplantation: new developments," Coronary Artery Disease, 8(5):305-316.

Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).

Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).

Lin et al., Jun. 2002, "Cytomegalovirus retinitis after initiation of highly active antiretroviral therapy in HIV infected patients: natural history and clinical predictors," Retina, 22(3):268-277.

Ljungman, Oct. 2002, "Beta-herpesvirus challenges in the transplant recipient," The Journal of Infectious Diseases, 186(Suppl 1):S99-S109.

Lu et al., Feb. 1997, "Adoptive transfer of murine cytomegalovirus-immune lymph node cells prevents retinitis in T-cell-depleted mice," Investigative Ophthalmology & Visual Science, 38:301-310.

Macesic et al., Mar. 2015, "Adoptive T cell immunotherapy for treatment of ganciclovir-resistant cytomegalovirus disease in a renal transplant recipient," American Journal of Transplantation, 15(3):827-832 (Published online Feb. 3, 2015).

Maul and Negorev, Jun. 2008, "Differences between mouse and human cytomegalovirus interactions with their respective hosts at immediate early times of the replication cycle," Medical Microbiology and Immunology, 197(2):241-249 (Published online Feb. 9, 2008).

Medawar, Feb. 1948, "Immunity to homologous grafted skin; the fate of skin homografts transplanted to the brain, to subcutaneous tissue, and to the anterior chamber of the eye," British journal of experimental pathology, 29(1):58-69.

Mocarski et al., Jan. 1993, "Human cytomegalovirus in a SCID-hu mouse: thymic epithelial cells are prominent targets of viral replication," Proceedings of the National Academy of Sciences of the United States of America, 90(1):104-108.

O'Reilly et al., May 2007, "Adoptive transfer of antigen-specific T-cells of donor type for immunotherapy of viral infections following allogeneic hematopoietic cell transplants," Immunologic Research, 38(1-3):237-250.

O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).

O'Reilly et al., Sep. 2011, "Novel strategies for adoptive therapy following HLA disparate transplants," Best Practice & Research Clinical Haematology, 24(3):381-391.

O'Reilly et al., Jun. 2015, "T-cell depleted allogeneic hematopoietic cell transplants as a platform for adoptive therapy with leukemia selective or virus-specific T-cells," Bone Marrow Transplant, 50(Suppl 2):S43-S50.

O'Reilly, meeting abstract for the oral presentation on Oct. 31, 2014 at The 76th Annual Meeting of the Japanese Society of Hematology, held Oct. 31-Nov. 2, 2014, Osaka, Japan.

Palella et al., Mar. 1998, "Declining morbidity and mortality among patients with advanced human immunodeficiency virus infection. HIV Outpatient Study Investigators," The New England Journal of Medicine, 338(13):853-860.

Palestine et al., Sep. 1984, "Ophthalmic involvement in acquired immunodeficiency syndrome," Ophthalmology, 91(9):1092-1099.

Papadopoulou et al., Jun. 2014, "Activity of broad-spectrum T cells as treatment for AdV, EBV, CMV, BKV, and HHV6 infections after HSCT," Science Translational Medicine, 6(242):242ra83.

Pecorella et al., Nov. 2000, "Postmortem histological survey of the ocular lesions in a British population of AIDS patients," British Journal of Ophthalmology, 84(11):1275-1281.

Pipeling et al., Dec. 2011, "Primary cytomegalovirus phosphoprotein 65-specific CD8+ T-cell responses and T-bet levels predict immune control during early chronic infection in lung transplant recipients," The Journal of Infectious Diseases, 204(11):1663-1671 (Published online Oct. 21, 2011).

Podlech et al., Sep. 1998, "Reconstitution of CD8 T cells is essential for the prevention of multiple-organ cytomegalovirus histopathology after bone marrow transplantation," Journal of General Virology, 79(Pt 9):2099-2104.

Pollard et al., Nov. 1980, "Cytomegalovirus retinitis in immunosuppressed hosts. I. Natural history and effects of treatment with adenine arabinoside," Annals of Internal Medicine, 93(5): 655-664.

"Primary transplant donor derived CMVpp65 specific T-cells for the treatment of CMV infection or persistent CMV viremia after allogeneic hematopoietic stem cell transplantation," ClinicalTrials.gov, accessed at http://www.clinicaltrials.gov/ct2/show/NCT01646645?term=NCT01646645&rank=1, first received on Jul. 18, 2012, accessed on Oct. 21, 2014, 4 pages.

Prockop et al., Dec. 2014, "Third party donor derived CMV specific T cells for the treatment of refractory CMV viremia and disease after hematopoietic stem cell transplant," Blood, 124(21):184.

Prockop et al., Dec. 2015, "Successful treatment of refractory CMV chorioretinitis and meningoencephalitis with adoptive transfer of third party CMVpp65 specific T-cell lines," Blood, 126(23):3157.

(56) References Cited

OTHER PUBLICATIONS

Prockop, "3rd party CMV specific T cells for the treatment of refractory CMV viremia and disease after HSCT," slide presentation on Dec. 7, 2014 at the 56th ASH Annual Meeting held Dec. 6-9, 2014, San Francisco, California, United States, 27 pages.

Prockop, "Adoptive immunotherapy with banked virus specific 3rd party donor T-cells for CMV infections and EBV LPD complicating hematopoietic cell transplants," slide presentation on Oct. 31, 2014 at the 76th Annual Meeting of the Japanese Society of Hematology, held Oct. 31-Nov. 2, 2014, Osaka, Japan, 43 pages.

Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.

Quinnan et al., Jul. 1982, "Cytotoxic t cells in cytomegalovirus infection: HLA-restricted T-lymphocyte and non-T-lymphocyte cytotoxic responses correlate with recovery from cytomegalovirus infection in bone-marrow-transplant recipients," The New England Journal of Medicine, 307(1):7-13.

Rao et al., 1998, "Role of retinal vascular endothelial cells in development of CMV retinitis," Transactions of the American Ophthalmological Society, 96:111-126.

Reddehase et al., Oct. 1987, "CD8-positive T lymphocytes specific for murine cytomegalovirus immediate-early antigens mediate protective immunity," Journal of Virology, 61(10):3102-3108.

Reddehase et al., Mar. 1988, "Adoptive immunotherapy of murine cytomegalovirus adrenalitis in the immunocompromised host: CD4-helper-independent antiviral function of CD8-positive memory T lymphocytes derived from latently infected donors," Journal of Virology, 62(3):1061-1065.

Riddell et al., Jul. 1992, "Restoration of viral immunity in immunodeficient humans by the adoptive transfer of T cell clones," Science, 257(5067):238-241.

Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.

Song et al., Jun. 2002, "Paradoxical activity of CMV retinitis in patients receiving highly active antiretroviral therapy," Retina, 22(3):262-267.

Sugar et al., Jun. 2012. "Incidence of cytomegalovirus retinitis in the era of highly active antiretroviral therapy," American Journal of Ophthalmology, 153(6):1016-1024 (Published online Feb. 4, 2012).

Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).

"Trial of third party donor derived CMVpp65 specific T-cells for the treatment of CMV infection or persistent CMV viremia after allogeneic hematopoietic stem cell transplantation," ClinicalTrials.gov, accessed at https://clinicaltrials.gov/ct2/show/NCT02136797?term=NCT02136797&rank=1, first received on May 9, 2014, accessed on Nov. 10, 2014, 4 pages.

Trivedi et al., Apr. 2005, "Generation of CMV-specific T lymphocytes using protein-spanning pools of pp65-derived overlapping pentadecapeptides for adoptive immunotherapy," Blood, 105(7):2793-2801 (Published online Oct. 28, 2004).

Uhlin et al., Oct. 2012, "Rapid salvage treatment with virus-specific T cells for therapy-resistant disease," Clinical Infectious Diseases, 55(8):1064-1073 (Published online Jul. 17, 2012).

Waldrop et al., Apr. 1997, "Determination of antigen-specific memory/effector CD4+ T cell frequencies by flow cytometry: evidence for a novel, antigen-specific homeostatic mechanism in HIV-associated immunodeficiency," Journal of Clinical Investigation, 99(7):1739-1750.

Walter et al., Oct. 1995, "Reconstitution of cellular immunity against cytomegalovirus in recipients of allogeneic bone marrow by transfer of T-cell clones from the donor," The New England Journal of Medicine, 333(16): 1038-1044.

Wang et al., Feb. 2005, "Human cytomegalovirus genes in the 15-kilobase region are required for viral replication in implanted human tissues in SCID mice," Journal of Virology, 79(4):2115-2123.

Weller, Dec. 1970, "Review. Cytomegaloviruses: the difficult years," The Journal of Infectious Diseases, 122(6):532-539.

Zhong et al., Sep. 2008, "Induction of pluripotent protective immunity following immunisation with a chimeric vaccine against human cytomegalovirus," PLoS One, 3(9):e3256.

\* cited by examiner

| | | HLA | | | | | | | | | CMV CTL Epitope | CMV CTL HLA Restriction | CTL Dose | # CTL Cycles | Response |
|---|---|---|---|---|---|---|---|---|---|---|---|---|---|---|---|
| | | A | | B | | C | | DR | | DQ | | | | | |
| 1 | Patient | 0101 | 0201 | 0801 | 4402 | 0701 | 1203 | 0301 | 1501 | 0201 | 0602 | NLVPMVATV | A0201 | 1 x 10^6/kg | 2 | CR |
| | CTL Donor | 0101 | 0201 | 3906 | 4402 | 0501 | 0501 | 0801 | 1104 | 0402 | 0301 | | | | | |
| 2 | Patient | 2902 | 7401 | 4501 | 1503 | 0602 | 0210 | 0901 | 1101 | 0202 | 0319 | VCSMENTRATK | A 2902 C 0602 | 1 x 10^6/kg | 1 | CR |
| | CTL Donor | 2902 | 2902 | 4501 | 4403 | 0602 | 1601 | 0301 | 1501 | 0201 | 0602 | | | | | |
| 3 | Patient | 3001 | 3002 | 1302 | 1516 | 1402 | 1604 | 1303 | 1502 | 0301 | 0601 | GIHVR VSQPS LILVS | A3001/ DRB1 0701 | 1 x 10^6/kg | 3 | Sustained PR - improvement in vision which remained stable |
| | CTL Donor | 0301 | 3001 | 1302 | 4101 | 0602 | 17/N/N | 0404 | 0701 | 0402 | 0202 | | | | | |
| 4 | Patient | 0205 | 3002 | 1801 | 5001 | 0501 | 0602 | 0301 | 1302 | 0201 | 0604 | NLVPMVATV | A 0201 | 1 x 10^6/kg | Single dose of CTLs | Not Evaluable |
| | CTL Donor | 0201 | 3201 | 0801 | 4403 | 0701 | 1601 | 0301 | 1301 | 0201 | 0603 | | | | | |
| 5 | Patient | 0301 | 3101 | 0702 | 4402 | 0501 | 0702 | 0401 | 1201 | 0301 | 0301 | TPRVTGGGAM RPHERNGFTV (minor) | B 0702 | 1 x 10^6/kg | 2 | CR |
| | CTL Donor | 0201 | 0101 | 0702 | 0801 | 0702 | 0701 | 0401 | 0401 | 0301 | 0301 | | | | | |
| 6 | Patient | 0205 | 1101 | 1501 | 5001 | 0303 | 0602 | 0701 | 0501 | 0202 | 0602 | GPISGHVLK/ SGKLFM HVTLG | A1101 / DRB1 0701 | 1 x 10^6/kg | 1 | CR |
| | CTL Donor | 1101 | 1101 | 5501 | 5501 | 0303 | 0303 | 0701 | 1401 | 0303 | 0503 | | | | | |

Figure 2

METHODS OF TREATING CMV RETINITIS BY T CELL THERAPY

CROSS-REFERENCE TO RELATED APPLICATIONS

This application claims the benefit of U.S. Provisional Patent Application Nos. 62/185,558, filed Jun. 26, 2015, and 62/191,304, filed Jul. 10, 2015, which are incorporated by reference herein in their entireties.

GOVERNMENT RIGHTS STATEMENT

This invention was made with government support under CA023766 and CA162002 awarded by National Institutes of Health, The government has certain rights in the invention.

1. FIELD

Disclosed herein are methods of treating CMV (cytomegalovirus) retinitis in a human patient in need thereof, comprising administering to the human patient a population of allogeneic T cells comprising CMV-specific T cells, wherein the human patient is infected with HIV or has been the recipient of a solid organ transplant.

2. BACKGROUND

CMV Induced Retinitis: Epidemiology, Clinical Features and Morbidity

Human CMV (HCMV) is a β herpesvirus which contains a dsDNA genome encoding >200 proteins (Chee et al., 1990, Curr Top Microbiol Immunol 154:125-169). HCMV infection usually develops asymptomatic lifelong infection in 50%-90% of healthy individuals, but can cause severe clinical complications when reactivated in immunocompromised patients (Ljungman, 2002, J Infect Dis: 186 Suppl 1:S99-S109; Fishman, 2007, N Engl J Med 357:2601-2614). One of the most serious HCMV-associated diseases in severely immunocompromised patients is the HCMV retinitis that leads to progressive loss of vision and blindness (Conboy et al., 1987, J Pediatr 111:343-348; Jabs et al., 1989, Ophthalmology 96:1092-1099; Jacobson and Mills, 1988, Ann Intern Med 108:585-594; Egbert et al., 1980, Ann Intern Med 93: 664-670; Pollard et al., 1980, Ann Intern Med 93: 655-664).

The incidence of HCMV retinitis in AIDS patients in the United States before the advent of highly active antiretroviral therapy (HAART), was estimated at 30% (Hoover et al., 1996, Arch Ophthalmol 114: 821-827), which has decreased to <10% in the post HAART era (Sugar et al., 2012. Am J Ophthalmol 153:1016-1024 e5; Palella et al., 1998, N Engl J Med 338:853-860; Jacobson et al., 2000, Clin Infect Dis 30:231-233). In children with symptomatic HCMV infection, an incidence of 5%-30% has been reported (Fowler et al., 1992, N Engl J Med 326:663-667). In severely iatrogenically immunosuppressed adult bone marrow transplant (BMT) recipients, one study has reported to have 10 HCMV retinitis cases of 5721 during a 14-year follow-up (Crippa et al., 2001, Clin Infect Dis 32:214-219). In solid organ transplant (SOT) recipients, a review of several studies has reported a total of 14 cases among 12,653 patients (Egli et al., 2008, Transpl Infect Dis 10:27-43). The clinical course for CMV retinitis can be protracted with prolonged periods of quiescence followed by progression. In HIV patients prior to HAART, CMV retinitis was associated with high rates of visual impairment (up to 98/100 eye-years (EYs]) and blindness (up to 49/100 EYs) (Holbrook et al., 2003, Arch Ophthalmol 121:99-107). In the modern era, treatment with antiretroviral agents can lead to suppression of the HIV RNA circulating in the blood (HIV load), thereby lending to immune recovery manifested as an increase in CD4+ T cells. Despite this dramatic decrease in the incidence of CMV retinitis and the improved outcomes due to modern antiretroviral therapy, CMV retinitis and vision loss from CMV retinitis continue to occur (Jabs et al., 2013, Ophthalmology 120:1262-1270; Jabs et al., 2010, Ophthalmology 117:2152-2161 e1-2), with the most recently reported rate of 0.9/100 person-year (Jabs et al., 2015, Ophthalmology pii:S0161-6420(15)00175-X, published online Apr. 16, 2015).

HCMV retinitis is diagnosed by ophthalmologic examination. Classic ophthalmologic findings of HCMV retinitis include white areas of retinal necrosis with associated hemorrhage and minimal vitreous inflammation (Lin et al., 2002, Retina 22:268-277). The current standard treatment of CMV retinitis consists of intravenous antiviral agents such as Ganciclovir and Foscarnet which are given at induction dosing for 2 weeks followed by maintenance dose of oral (Valganciclovir) or IV therapy for several weeks based on detection of CMV DNA in the blood or ophthalmologic evaluation. In patients failing to respond to these agents, cidofovir can be effective in clearing viremia or inducing regression of disease. Timely institution of treatment is critical, and in such cases approximately 50-60% of the patients will have either improvement or stabilization in visual acuity, while 40% of the patients will have progressive decline in vision (Eid et al., 2008, Transpl Infect Dis 10:13-18). Responses vary between the groups of patients depending on the underlying disease and level of immune suppression. The treatment is discontinued once there is evidence of reconstitution of T cell immunity. For patients who have ongoing immune suppression such as solid organ transplant recipients or AIDS patients with mid to higher level viral loads, current antiviral therapies carry significant toxicities when administered for prolonged periods. Therefore, additional therapies are needed for patients failing to respond, or for those who have continuous ongoing immune suppression.

Early studies in experimental mouse models provided the first evidence for the protective effect of adoptively transferred virus specific CD8 T cells against lethal, multiple-organ CMV infection. These studies used as immunocompromised host, BALB/c mice treated with hematoablative total-body irradiation, followed by intravenous adoptive transfer of CMV-primed CD8+ T cells and intra-plantar infection with murine CMV (MCMV) (Reddehase et al., 1988, J Virol 62:1061-1065; Reddehase et al., 1987, J Virol 61:3102-3108). Several subsequent studies defined the epitope specificities involved in protection against murine CMV and the additive effects of adoptively transferred CD4+ T-cells.

In humans, Riddell et al. first demonstrated the efficacy of adoptively transferred CMV-specific CD8 T-cell clones derived from the transplant donor prophylactically administered to recipients of BMT (bone marrow transplant) at risk for CMV infection (Riddell et al., 1992, Science 257:238-241; Walter et al., 1995, N Engl J Med 333:1038-1044). The efficacy of donor derived CMV-specific T-cells for the treatment of CMV viremia and disease was subsequently demonstrated (Einsele et al., 2002, Blood 99:3916-3922; Feuchtinger et al., 2010, Blood 116:4360-4367; Koehne et al., 2015, Biol Blood Marrow Transplant pii: S1083-8791 (15)00372-9, published online May 29, 2015; Peggs et al., 2003, Lancet 362:1375-1377). Importantly, these initial trials demonstrated that CMV-specific T-cells can effectively treat CNS infections like encephalitis (Einsele et al., 2002, Blood 99:3916-3922; Feuchtinger et al., 2010, Blood 116: 4360-4367), suggesting that these T-cells can penetrate the blood brain barrier. Similarly, in the treatment of Epstein-Barr virus related lymphoproliferative diseases (EBV-LPDs) developing in BMT recipients, it has been previously shown that adoptively transferred transplant donor derived EBV-specific T-cells can cause complete regressions of CNS lymphomas, providing evidence that adoptively transferred T-cells can home to the CNS (central nervous system) (Doubrovina et al., 2012, Blood 119:2644-2656).

Further advancements in this field evolved to address specific limitations of this therapy that would limit broad application of this treatment such as; the lack of timely availability of donor derived virus specific T-cells and the inability to generate cells from seronegative and cord blood donors. To overcome this limitation, pre-generated third party donor derived virus specific T-cells could be readily available for treatment of serious viral infections in such patients. Several groups have demonstrated the safety and potential efficacy of third party donor derived virus specific T cells for the treatment of EBV (Epstein-Barr virus), CMV and adenovirus infections in BMT and SOT (solid organ transplant) recipients (Hague et al., 2007, Blood 110:1123-1131; Leen et al., 2013, Blood 121:5113-5123).

Retina as an Immune Privilege Site: Pathogenesis and Implications for Treatment

The term 'immune-privileged site' was created in the 1940s by Sir Peter Medawar (Medawar, 1948, Br J Exp Pathol 29:58-69). In 1977, Barker and Billingham used this term to express the exemption of sites (such as the brain, ovary, testis, pregnant uterus, placenta, eye and the hamster cheek pouch) from immune responses (Barker and Billingham, 1977, Adv Immunol 25:1-54). Similarly, pathogen-mediated ocular inflammation can be harmful to the eye. Since minor inflammation can result in impaired vision or even blindness, the eye is naturally designed as an immune privileged site where infections usually do not lead to destructive immune reactions (Griffith et al., 1995, Science, 270:1189-1192). The underlying mechanism has been hypothesized to involve Fas ligand (FasL)-mediated programmed cell death (also called apoptosis) of Fas (CD95)-expressing T cells when attracted to the infection sites (Griffith et al., 1995, Science, 270:1189-1192). In this case, activated T cells are eliminated through ligation of Fas by FasL and no serious immune reactions are induced. TGF β is another cytokine present in the eye that inhibits Th1 cytokine mediated tissue destruction (Gabrielian et al., 1994, Invest Ophthalmol Vis Sci 35:4253-4259). Thus, the damage to the eye is minimized. However, CMV infection of human eyes is shown to cause large-scaled cell death and tremendous visual dysfunction (Jabs et al., 1989, Ophthalmology 96:1092-1099; Jacobson and Mills, 1988, Ann Intern Med 108:585-594).

The retina is anatomically protected from invading pathogens or inflammatory cells by the inner and outer blood-retina barrier. The inner blood-retina barrier consists of microvascular endothelial cells and the outer blood-retina barrier consists of RPE (retinal pigment epithelium) cells. Both cell types form functional tight junctions and are responsible for selective transport of essential molecules and for keeping out unwanted pathogens or activated leukocytes. It has been suggested that, in CMV infection, the internal blood-retinal barrier is disrupted after primary CMV replication in endothelial cells, allowing CMV particles to reach retinal glial cells. Subsequently, CMV might spread towards the RPE (Rao et al., 1998, Trans Am Ophthalmol Soc 96:111-126). Although glial cells, microvascular endothelial cells and RPE cells are major targets of CMV infection in the eye, all 10 layers of the retina are sites of necrotic lesions (Rao et al., 1998, Trans Am Ophthalmol Soc 96:111-126; Pecorella et al., 2000, Br J Ophthalmol 84:1275-1281; Palestine et al., 1984, Ophthalmology 91:1092-1099).

These anatomic and physiological features of the retina are thought to contribute to the characteristic features of CMV retinitis that are distinct from CMV infections in other organs; such as the occurrence of retinitis later in the course of infection or immunosuppression, in the absence of CMV viremia, and as a paradoxical infection occurring despite reconstitution of CD4+ T-cell count (Song et al., 2002, Retina 22:262-267). The same anatomical features can also potentially limit the efficacy of systemically administered anti-viral agents. For example, systemic CMV infections can be successfully treated with the anticytomegalovirus drugs ganciclovir, foscarnet or cidofovir, except in cases infected with ganciclovir resistant CMV strains. However, in some cases of retinitis, disease progression has been observed despite continuous antiviral therapy and proven drug sensitivity of isolated virus strains, suggesting that adequate drug concentrations of systemically administered drugs may not be achieved in the eye. Protocols for intravitreal administration of ganciclovir and foscarnet have therefore been implemented for treatment of CMV retinitis.

T-cell Immunity and CMV Infection

The adaptive immune system, particularly CD8+ T cells, plays a key role in the control of acute viral infections, including CMV infection (Crough and Khanna, 2009, Clin Microbiol Rev 22:76-98, Table of Contents). Viral-specific effector CD8+ T cells exert their antiviral activities through the production of type 1 cytokines such as interferon γ (IFN-γ) and tumor necrosis factor α (TNF-α), as well as through their antigen specific cytolytic activity. In both mouse models and in humans, reconstitution of CMV-specific CD8+ and CD4+ T-cells is critical for the control of CMV viremia and infections in recipients of both bone marrow (Quinnan et al., 1982, N Engl J Med 307:7-13; Hakki et al., 2003, Blood 102:3060-3067; Podlech et al., 1998, J Gen Virol 79:2099-2104) and solid organ transplants (Kumar et al., 2009, Am J Transplant 9:1214-1222; Pipeling et al., 2011, J Infect Dis 204:1663-1671).

CMV retinitis also occurs in patients with compromised cellular immunity, and in a proportion of patients, development of retinitis is associated with prior or concurrent reactivation of CMV in blood as well as other CMV end organ disease such as colitis or pneumonitis (Eid et al., 2008, Transpl Infect Dis 10:13-18). However, the median time to onset of retinitis is 6-12 months after initiation of immunosuppression or after transplant (Fishman, 2007, N Engl J Med 357:2601-2614; Crippa et al., 2001, Clin Infect Dis 32:214-219), which is a later time when the full effect of immunosuppressive medications in recipients of solid organ transplants are well established. For HIV patients, the primary clinical parameters determining risk for development of CMV retinitis are the post-HAART HIV viral load and CD4+ T helper cell counts ≤100/μl (Lin et al., 2002, Retina 22:268-277). CMV retinitis in HIV-positive patients also occurs later than CMV-associated conditions in other organs (colon, lungs, liver) affected by CMV infection. Furthermore, the T-cell response may also contribute to ocular pathology induced by CMV, as reflected by the development of uveitis in HIV patients at the time of CD4 T-cell recovery following institution of HAART therapy.

Taken together, these findings suggest that the rarity and late incidence of chorioretinitis reflect the profound degree of T-cell deficiency together with the resistance created by an intact blood-retinal barrier.

Earlier studies in murine CMV retinitis models have suggested that adoptive transfer of CMV-specific CD8+ T-cells could be protective against CMV retinitis developing in immunocompromised mice (Bigger et al., 1999, Invest Ophthalmol Vis Sci 40:2608-2613; Lu et al., 1997, Invest Ophthalmol Vis Sci 38:301-310). These studies used immunocompromised mice (thymectomized and T-cell depleted BALB/c mice) in whom retinitis was artificially induced by injecting infectious virus directly into the eye via the superciliary route, and groups of animals were infused with murine CMV-specific T-cells or control T-cells 2 hours prior to injection of virus. Although this model yielded the phenotypic and pathologic characteristics of CMV induced retinitis, this model is highly non-physiological, and the results cannot be extrapolated to the human retinitis treatment for several reasons. (1) In contrast to the mouse model in which CMV is injected directly into the eye, the intact retinal barrier is normally difficult to disrupt, and retinal human CMV infection develops through the retinal endothelium and occurs several months after immunosuppression, (2) The T-cells were transferred at the time of introduction of the infection in the murine model, while in human patients developing CMV retinitis, CMV-specific T-cells would be deficient or at least non-functional for some time (detailed above), and lastly (3) CMV is highly species specific. Early studies after isolation of murine and human cytomegaloviruses had observed that MCMV could not be propagated in human tissue and HCMV did not replicate in murine cells (Weller, 1970, J Infect Dis 122:532-539). After further exploration, it has been generally accepted that the cytomegaloviruses are highly species specific: Each virus replicates only in cells of its own or closely related host species. Therefore, murine CMV (MCMV) is not analogous to human CMV. There are also significant differences in the clinical spectrum of MCMV infection in that transplacental infection does not occur with MCMV, and even artificial introduction of MCMV at early stages of embryonic development does not result in CNS infection in mice, while human congenital CMV causes significant neurological sequelae. MCMV has been extensively studied and investigated for the potential use of this virus as a stand-in for human CMV (HCMV) to develop a mouse model, primarily for preclinical studies for vaccine strategies against human CMV, specifically to prevent congenital CMV infections. However, a chief limitation of the MCMV model for testing vaccines against congenital CMV infection has been the inability of the virus to infect the fetus by transplacental route, suggesting that MCMV causes a different spectrum of disease than HCMV. Although the precise molecular/cellular basis for the species-specificity of CMV remains unknown, studies by Maul et al. and others have shown that there are specific differences in the genes encoding the immediate early 1, 2 and 3 proteins of the MCMV and HCMV viruses, which have differential effects on the host cell transcriptional repressor Fax as well histone deacetylase, thereby affecting their ability for host infection (Maul and Negorev, 2008, Med Microbiol Immunol 197:241-249). These differences may also affect the host immune response to the virus, rendering this model less applicable to evaluation of immunotherapies for human CMV.

In order to overcome the species specificity of CMV infection, investigators have used human tissue explants; fetal thymus/liver (Mocarski et al., 1993, Proc Natl Acad Sci USA 90:104-108; Wang et al., 2005, J Virol 79:2115-2123; Brown et al., 1995, J Infect Dis 171:1599-1603) or fetal retinal tissue implants (Bidanset et al., 2001, J Infect Dis 184:192-195) maintained in SCID/hu mice that could allow the inoculation and propagation of HCMV in human cells which could then be used to test antiviral drugs or other therapeutic interventions specific for HCMV. Although these models are somewhat useful in evaluation of antiviral drugs (Kern, 2006, Antiviral Res 71:164-171), there is less information about exploiting the SCID/hu implant model for evaluation of HCMV vaccines and immunotherapies. Khanna and colleagues studied vaccine responses in a small animal model, in which HLA-2 transgenic mice immunized with replication-deficient adenovirus vectors expressing HCMV epitopes were used as a way to overcome species specificity of CMV viruses (Zhong et al., 2008, PLoS One 3:e3256). This chimeric vaccine demonstrated strong HCMV-specific CD8+ and CD4+ T-cell responses, as well as virus-neutralizing antibody. Although not a true "HCMV challenge" in a heterologous animal model, these experiments nevertheless represent an innovative approach to overcoming the problem of species specificity in CMV vaccine models.

Thus far it is clear that CMV retinitis exclusively occurs in patients with deficient T-cell immunity. In bone marrow transplant recipients, it has been reported that adoptive transfer of transplant donor derived or third party donor derived CMV specific T-cells restores T-cell immunity against CMV infection of the CNS such as encephalitis (Koehne et al., 2015, Biol Blood Marrow Transplant S1083-8791(15)00372-9, published online May 29, 2015; Feuchtinger et al., 2010, Blood 116:4360-4367), and in some cases of CMV retinitis (Gupta et al., 2015, Ophthalmic Surg Lasers Imaging Retina 46:80-82). Since third party donor derived T-cells have a limited survival after infusion before they undergo immune rejection within the allogeneic recipient, this approach may be used for bridging anti-CMV T-cell immunity in recipients of bone marrow transplants until reconstitution of T-cell immunity. However, there are specific differences in host physiology and CMV infection between recipients of solid organ transplant (SOT) and HIV-infected patients on one hand, and bone marrow transplant recipients on the other hand, because of which data from BMT recipients cannot be extrapolated to these two groups of patients. First of all, in recipients of SOT, CMV reactivation and original infection occurs within the donor cells (Hammond et al., 2013, Transpl Infect Dis 15:163-170; Harvala et al., 2013, J Med Virol 85:893-898), while BMT recipients experience host CMV reactivation. The infusion of third party CMV specific T-cells in SOT would thus carry the potential risk of precipitating immune rejection of the transplanted tissue carrying the CMV infection. Furthermore, independent of other factors, the inflammatory response resulting from CMV infection in SOT recipients could also trigger a rejection episode by enhancing antigen presentation, thus potentially placing these patients at high risk of organ allograft rejection by this treatment approach. Secondly, SOT recipients and HIV-infected patients have an indefinite period of immunodeficiency because of immunosuppressive therapy to prevent rejection, or variable CD4 count recovery with or without HAART therapy, respectively. In contrast, BMT recipients have a finite period of immunodeficiency in the absence of GvHD (graft-versus-host disease). This would necessitate multiple ongoing doses of CMV specific T-cells to treat CMV infection in SOT and HIV-infected patients, which could potentially compound the risk of allograft rejection in SOT recipients and immune recovery uveitis in HIV-infected patients. The efficacy of T cell therapy could also potentially be compromised by the lack of adequate number of T-cell doses in SOT recipients and HIV-infected patients.

Therefore, while there is a need for additional therapies for the treatment of CMV retinitis in human patients who are infected with HIV or who have been solid organ transplant recipients, these previous studies mentioned above have limited applicability.

Citation of a reference herein shall not be construed as an admission that such is prior art to the present disclosure.

3. SUMMARY OF THE INVENTION

The present invention relates to methods of treating CMV (cytomegalovirus) retinitis in a human patient who is infected with HIV. The present invention further relates to methods of treating CMV retinitis in a human patient who has been the recipient of a solid organ transplant.

In one aspect, provided herein are methods of treating CMV retinitis in a human patient in need thereof, comprising administering to the human patient a population of allogeneic T cells comprising CMV-specific T cells; wherein the human patient is infected with HIV. In various embodiments, the human patient has AIDS (acquired immune deficiency syndrome).

In another aspect, provided herein are methods of treating CMV retinitis in a human patient in need thereof, comprising administering to the human patient a population of allogeneic T cells comprising CMV-specific T cells; wherein the human patient has been the recipient of a solid organ transplant from a transplant donor.

In various embodiments, the population of allogeneic T cells that is administered to the human patient is restricted by an HLA allele shared with at least some, optionally all, of the CMV-infected cells (e.g., the infected cells of the retina).

In certain embodiments, preferably in addition to being restricted by an HLA allele shared with at least some, optionally all, of the CMV-infected cells (e.g., the infected cells of the retina), the population of allogeneic T cells comprising CMV-specific T cells shares at least 2 out of 8 HLA alleles (e.g., two HLA-A alleles, two HLA-B alleles, two HLA-C alleles, and two HLA-DR alleles) with at least some, optionally all, of the CMV-infected cells (e.g., the infected cells of the retina).

In specific embodiments, the methods of treating CMV retinitis described herein further comprise prior to the administering step a step of ascertaining at least one HLA allele of the human patient by high-resolution typing.

In various embodiments, the methods of treating CMV retinitis further comprise prior to the administering step a step of generating the population of allogeneic T cells in vitro.

In certain embodiments, the step of generating the population of allogeneic T cells in vitro comprises sensitizing (i.e., stimulating) allogeneic T cells to one or more CMV antigens so as to produce CMV-specific T cells.

In certain embodiments, the step of generating the population of allogeneic T cells in vitro comprises sensitizing allogeneic T cells using dendritic cells (preferably, the dendritic cells are derived from the donor of allogeneic T cells). In specific embodiments, the step of sensitizing allogeneic T cells using dendritic cells comprises loading the dendritic cells with at least one immunogenic peptide derived from one or more CMV antigens. In specific embodiments, the step of sensitizing allogeneic T cells using dendritic cells comprises loading the dendritic cells with a pool of overlapping peptides derived from one or more CMV antigens.

In certain embodiments, the step of generating the population of allogeneic T cells in vitro comprises sensitizing allogeneic T cells using cytokine-activated monocytes (preferably, the cytokine-activated monocytes are derived from the donor of allogeneic T cells). In specific embodiments, the step of sensitizing allogeneic T cells using cytokine-activated monocytes comprises loading the cytokine-activated monocytes with at least one immunogenic peptide derived from one or more CMV antigens. In specific embodiments, the step of sensitizing allogeneic T cells using cytokine-activated monocytes comprises loading the cytokine-activated monocytes with a pool of overlapping peptides derived from one or more CMV antigens.

In certain embodiments, the step of generating the population of allogeneic T cells in vitro comprises sensitizing allogeneic T cells using peripheral blood mononuclear cells (preferably, the peripheral blood mononuclear cells are derived from the donor of allogeneic T cells). In specific embodiments, the step of sensitizing allogeneic T cells using peripheral blood mononuclear cells comprises loading the peripheral blood mononuclear cells with at least one immunogenic peptide derived from one or more CMV antigens. In specific embodiments, the step of sensitizing allogeneic T cells using peripheral blood mononuclear cells comprises loading the peripheral blood mononuclear cells with a pool of overlapping peptides derived from one or more CMV antigens.

In certain embodiments, the step of generating the population of allogeneic T cells in vitro comprises sensitizing allogeneic T cells using an EBV-transformed B lymphocyte cell line (EBV-BLCL). In specific embodiments, the step of sensitizing allogeneic T cells using an EBV-BLCL comprises loading the EBV-BLCL cells with at least one immunogenic peptide derived from one or more CMV antigens. In specific embodiments, the step of sensitizing allogeneic T cells using an EBV-BLCL comprises loading the EBV-BLCL cells with a pool of overlapping peptides derived from one or more CMV antigens.

In certain embodiments, the step of generating the population of allogeneic T cells in vitro comprises sensitizing allogeneic T cells using artificial antigen-presenting cells (AAPCs). In specific embodiments, the step of sensitizing allogeneic T cells using AAPCs comprises loading the AAPCs with at least one immunogenic peptide derived from one or more CMV antigens. In specific embodiments, the step of sensitizing allogeneic T cells using AAPCs comprises loading the AAPCs with a pool of overlapping peptides derived from one or more CMV antigens. In specific embodiments, the step of sensitizing allogeneic T cells using AAPCs comprises engineering the AAPCs to express at least one immunogenic CMV peptide or protein in the AAPCs.

In a specific embodiment, the pool of overlapping peptides is a pool of overlapping pentadecapeptides.

In specific embodiments, the methods of treating CMV retinitis described herein further comprise, after sensitizing, cryopreserving the allogeneic T cells.

In specific embodiments, the methods of treating CMV retinitis described herein further comprise, before the administering step, steps of thawing cryopreserved CMV-antigen sensitized allogeneic T cells, and expanding the allogeneic T cells in vitro, to produce the population of allogeneic T cells.

In certain embodiments, the methods of treating CMV retinitis described herein further comprise, before the administering step, a step of thawing a cryopreserved form of the population of allogeneic T cells.

In various embodiments, the population of allogeneic T cells is derived from a T cell line. In certain embodiments, the methods of treating CMV retinitis described herein further comprise, before the administering step, a step of selecting the T cell line from a bank of a plurality of cryopreserved T cell lines (preferably each comprising CMV-specific T cells). In certain embodiments, the methods of treating CMV retinitis described herein further comprise, before the administering step, a step of thawing a cryopreserved form of the T cell line. In specific embodiments, the methods of treating CMV retinitis described herein further comprises, before the administering step, a step of expanding the T cell line (for example, after thawing a cryopreserved form of the T cell line) in vitro.

In specific embodiments, the CMV-specific T cells administered in accordance with the methods described herein recognize CMVpp65.

In specific embodiments, the CMV-specific T cells administered in accordance with the methods described herein recognize CMV IE1.

In specific embodiments, the population of allogeneic T cells has not been transduced ex vivo with a gene that encodes a CMV-specific T-cell receptor.

In specific embodiments, at least some, optionally all, of the cells of the population of allogeneic T cells are rapamycin-sensitive.

In specific embodiments, the population of allogeneic T cells is not administered in combination with a PD-1 antagonist.

In certain embodiments, the administering is by infusion of the population of allogeneic T cells. In some embodiments, the infusion is bolus intravenous infusion.

In certain embodiments, the administering comprises administering at least about $1 \times 10^5$ T cells of the population of allogeneic T cells per kg per dose per week to the human patient. In some embodiments, the administering comprises administering about $1 \times 10^6$ to about $2 \times 10^6$ T cells of the population of allogeneic T cells per kg per dose per week to the human patient. In a specific embodiment, the administering comprises administering about $1 \times 10^6$ T cells of the population of allogeneic T cells per kg per dose per week to the human patient. In another specific embodiment, the administering comprises administering about $2 \times 10^6$ T cells of the population of allogeneic T cells per kg per dose per week to the human patient.

In certain embodiments, the methods of treating CMV retinitis described herein comprise administering at least 2 doses of the population of allogeneic T cells to the human patient. In specific embodiments, the methods of treating CMV retinitis described herein comprise administering 2, 3, 4, 5, or 6 doses of the population of allogeneic T cells to the human patient.

In certain embodiments, the methods of treating CMV retinitis described herein comprise administering a first cycle of one dose per week of the population of allogeneic T cells for 3 consecutive weeks followed by a washout period during which no dose of the population of allogeneic T cells is administered, followed by a second cycle of the one dose per week of the population of allogeneic T cells for 3 consecutive weeks. In specific embodiments, the methods of treating CMV retinitis described herein comprise administering two, three, four, five, or six cycles of one dose per week of the population of allogeneic T cells for 3 consecutive weeks, each cycle separated by a washout period during which no dose of the population of allogeneic T cells is administered. In a specific embodiment, the washout period is about three weeks.

In certain embodiments, the methods of treating CMV retinitis further comprise, after administering to the human patient the population of allogeneic T cells, administering to the human patient a second population of allogeneic T cells comprising CMV-specific T cells; wherein the second population of allogeneic T cells is restricted by a different HLA allele shared with at least some, optionally all, of the CMV-infected cells. In a specific embodiment, the methods of treating CMV retinitis comprise administering a first cycle of one dose per week of the population of allogeneic T cells for 3 consecutive weeks followed by a washout period during which no dose of the population of allogeneic T cells is administered, followed by a second cycle of one dose per week of the second population of allogeneic T cells for 3 consecutive weeks. In a further specific embodiment, the washout period is about three weeks. In certain embodiments, the human patient has no response, an incomplete response, or a suboptimal response (i.e., the human patient may still have a substantial benefit from continuing treatment, but has reduced chances of optimal long-term outcomes) after administering the population of allogeneic T cells and prior to administering the second population of allogeneic T cells.

In specific embodiments, the human patient has an active, not latent, CMV infection.

In specific embodiments, a CMV in the human patient has at least one mutation in its genome that confers resistance to one or more anti-viral agents. In a specific embodiment, the one or more anti-viral agents are selected from the group consisting of ganciclovir, foscarnet, valganciclovir, cidofovir, leflunomide, and combinations thereof In a specific embodiment, the mutation is in the UL97 gene. In another specific embodiment, the mutation is in the UL54 gene. In another specific embodiment, a first mutation is in the UL97 gene and a second mutation is in the UL54 gene.

In certain embodiments, the human patient has been the recipient of a solid organ transplant from a transplant donor. In specific embodiments, the solid organ transplant that the human patient has received is a kidney transplant, a liver transplant, a heart transplant, an intestinal transplant, a pancreas transplant, a lung transplant, a small bowel transplant, or a combination thereof. In a specific embodiment, the solid organ transplant that the human patient has received is a kidney transplant. In specific embodiments wherein the human patient has been the recipient of a solid organ transplant from a transplant donor, the population of allogeneic T cells is derived from a donor other than the transplant donor.

In specific embodiments, the human patient has not been the recipient of a hematopoietic stem cell transplant (e.g., a bone marrow transplant, a peripheral blood stem cell transplant, or a cord blood transplant).

In specific embodiments, the human patient has failed a previous therapy to treat the CMV retinitis. In a specific embodiment, the CMV retinitis is resistant to the previous therapy. In a specific embodiment, the human patient has been taken off the previous therapy due to intolerance of the therapy. In specific embodiments, the previous therapy is treatment with at least one anti-viral agent. In a specific embodiment, the at least one anti-viral agent is selected from the group consisting of ganciclovir, foscarnet, valganciclovir, cidofovir, leflunomide, and combinations thereof.

In specific embodiments, the methods of treating CMV retinitis further comprise concurrently treating the human patient with an anti-viral compound to treat the CMV retinitis. In a specific embodiment, the anti-viral compound is selected from the group consisting of ganciclovir, foscarnet, valganciclovir, cidofovir, leflunomide, and combinations thereof.

In specific embodiments, the methods of treating CMV retinitis further comprise prior to said administering step a step of genotyping a CMV of the human patient

4. BRIEF DESCRIPTION OF FIGURES

FIG. 2 is a summary of patients treated with third party donor-derived CMV-specific T cells.

Figure 4:
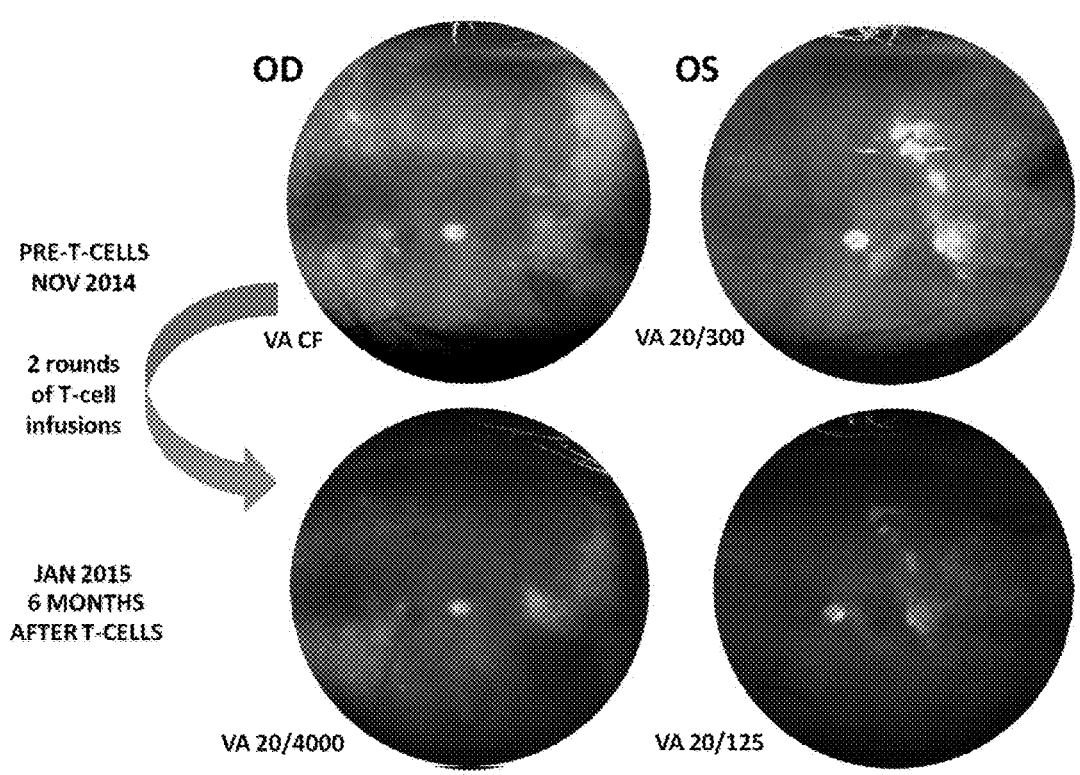

FIG. 4 shows the ophthalmologic examination results and Fundus photography of patient #5 before and after T cell therapy. VA: visual acuity. CF: count fingers. OD: oculus dexter, i.e., right eye. OS: oculus sinister, i.e., left eye.

Figure 5:
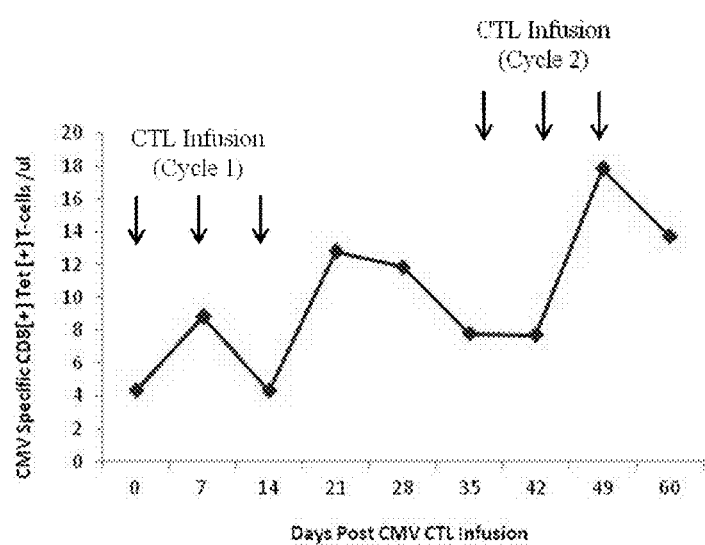

FIG. 5 shows a representative example (patient #5) illustrating that increases in CMV-specific T cells were associated with decline in CMV viral load in blood.

5. DETAILED DESCRIPTION

The present invention relates to methods of treating CMV (cytomegalovirus) retinitis in a human patient who is infected with HIV. The present invention further relates to methods of treating CMV retinitis in a human patient who has been the recipient of a solid organ transplant. The invention provides a T cell therapy method that is effective in treating CMV retinitis in a human patient with low or no toxicity, wherein the human patient is infected with HIV or has been the recipient of a solid organ transplant.

In one aspect, provided herein are methods of treating CMV retinitis in a human patient in need thereof, comprising administering to the human patient a population of allogeneic T cells comprising CMV-specific T cells; wherein the human patient is infected with HIV. In various embodiments, the human patient has AIDS (acquired immune deficiency syndrome).

In another aspect, provided herein are methods of treating CMV retinitis in a human patient in need thereof, comprising administering to the human patient a population of allogeneic T cells comprising CMV-specific T cells; wherein the human patient has been the recipient of a solid organ transplant from a transplant donor.

5.1. A Population of Allogeneic T Cells Restricted by an Shared HLA Allele with the Infected Cells of CMV Retinitis According to the invention, a population of allogeneic T cells comprising CMV-specific T cells is administered to the human patient. In a specific embodiment, the population of allogeneic T cells that is administered to the human patient is restricted by an HLA allele shared with at least some, optionally all, of the CMV-infected cells (e.g., the infected cells of the retina). Preferably, the population of allogeneic T cells has demonstrated anti-CMV cytotoxic activity, measured by a method known in the art (for example, as described in Trivedi et al., 2005, Blood 105:2793-2801; or Hasan et al., 2009, J Immunol 183: 2837-2850).

When the human patient is infected with HIV, the CMV-infected cells have the same HLA type (i.e., assignment) as the human patient. In specific embodiments when the human patient is infected with HIV, the population of allogeneic T cells that is administered to the human patient is restricted by an HLA allele shared with all of the CMV-infected cells. In some embodiments, this HLA allele restriction is ensured by ascertaining the HLA assignment of the CMV-infected cells, and selecting a population of allogeneic T cells comprising CMV-specific T cells (or a T cell line from which to derive the population of allogeneic T cells) restricted by an HLA allele of such CMV-infected cells. In other embodiments, when ascertaining the HLA assignment of the CMV-infected cells is not possible (or is possible but not performed), this HLA allele restriction is ensured by ascertaining the HLA assignment of the human patient (e.g., by using non-infected cells or tissue from the human patient), and selecting a population of allogeneic T cells comprising CMV-specific T cells (or a T cell line from which to derive the population of allogeneic T cells) restricted by an HLA allele of the human patient.

When the human patient has been the recipient of a solid organ transplant from a transplant donor, the CMV-infected cells in most cases contain both infected cells of the patient origin and infected cells of the transplant donor origin. In specific embodiments when the human patient has been the recipient of a solid organ transplant, the population of allogeneic T cells that is administered to the human patient can be restricted by an HLA allele shared with all of the CMV-infected cells. In specific embodiments when the human patient has been the recipient of a solid organ transplant, the population of allogeneic T cells that is administered to the human patient can be restricted by an HLA allele shared with at least some of the CMV-infected cells. In some embodiments, a population of allogeneic T cells comprising CMV-specific T cells (or a T cell line from which to derive the population of allogeneic T cells) restricted by an HLA allele shared by both the human patient and the transplant donor is selected for administering (the population of allogeneic T cells that is administered to the human patient is then restricted by an HLA allele shared with all of the CMV-infected cells). In a specific embodiment when the human patient is at a high risk for organ allograft rejection, and CMV retinitis is the main problem without CMV viremia, a population of allogeneic T cells comprising CMV-specific T cells (or a T cell line from which to derive the population of allogeneic T cells) restricted by an HLA allele of the human patient can be selected for administering (the population of allogeneic T cells that is administered to the human patient is then restricted by an HLA allele shared with at least some of the CMV-infected cells). In a specific embodiment (e.g., when the origin of the CMV-infected cells is determined to be the human patient only), a population of allogeneic T cells comprising CMV-specific T cells (or a T cell line from which to derive the population of allogeneic T cells) restricted by an HLA allele of the human patient is selected for administering. In a specific embodiment (e.g., when the origin of the CMV-infected cells is determined to be the transplant donor only), a population of allogeneic T cells comprising CMV-specific T cells (or a T cell line from which to derive the population of allogeneic T cells) restricted by an HLA allele of the transplant donor is selected for administering. In some embodiments wherein the patient has CMV viremia, a population of allogeneic T cells comprising CMV-specific T cells (or a T cell line from which to derive the population of allogeneic T cells) that is restricted by an HLA allele shared by both the human patient and the transplant donor can be selected for administering. In certain embodiments, the methods further comprise prior to the administering step, a step of ascertaining the HLA assignment of the CMV-infected cells, the human patient, the transplant donor, or both the human patient and the transplant donor (as the case may be).

The origin of the CMV-infected cells can be determined by any method known in the art, for example, by analyzing variable tandem repeats (VTRs) (which is a method that uses unique DNA signature of small DNA sequences of different people to distinguish between the recipient and the donor of a transplant), or by looking for the presence or absence of chromosome Y if the donor and the recipient of a transplant are of different sexes (which is done by cytogenetics or by FISH (fluorescence in situ hybridization)).

In some embodiments of ascertaining an HLA assignment, at least 4 HLA loci (preferably HLA-A, HLA-B, HLA-C, and HLA-DR) are typed. In some embodiments of ascertaining an HLA assignment, 4 HLA loci (preferably HLA-A, HLA-B, HLA-C, and HLA-DR) are typed. In some embodiments of ascertaining an HLA assignment, 6 HLA loci are typed. In some embodiments of ascertaining an HLA assignment, 8 HLA loci are typed.

In certain embodiments, preferably in addition to being restricted by an HLA allele shared with at least some, optionally all, of the CMV-infected cells (e.g., the infected cells of the retina), the population of allogeneic T cells comprising CMV-specific T cells shares at least 2 HLA alleles with at least some, optionally all, of the CMV-infected cells (e.g., the infected cells of the retina). Preferably, the population of allogeneic T cells has demonstrated anti-CMV cytotoxic activity, measured by a method known in the art (for example, as described in Trivedi et al., 2005, Blood 105:2793-2801; or Hasan et al., 2009, J Immunol 183: 2837-2850). In specific embodiments, the population of allogeneic T cells comprising CMV-specific T cells shares at least 2 out of 8 HLA alleles (for example, two HLA-A alleles, two HLA-B alleles, two HLA-C alleles, and two HLA-DR alleles) with at least some, optionally all, of the CMV-infected cells.

When the human patient is infected with HIV, the CMV-infected cells have the same HLA type (i.e., assignment) as the human patient. In specific embodiments when the human patient is infected with HIV, the population of allogeneic T cells that is administered to the human patient shares at least 2 HLA alleles with all of the CMV-infected cells. In some embodiments, this sharing is ensured by ascertaining the HLA assignment of the CMV-infected cells, and selecting a population of allogeneic T cells comprising CMV-specific T cells (or a T cell line from which to derive the population of allogeneic T cells) that shares at least 2 (e.g., at least 2 out of 8) HLA alleles with such CMV-infected cells. In other embodiments, when ascertaining the HLA assignment of the CMV-infected cells is not possible (or is possible but not performed), this sharing is ensured by ascertaining the HLA assignment of the human patient (e.g., by using non-infected cells or tissue from the human patient), and selecting a population of allogeneic T cells comprising CMV-specific T cells (or a T cell line from which to derive the population of allogeneic T cells) that shares at least 2 (e.g., at least 2 out of 8) HLA alleles with the human patient.

When the human patient has been the recipient of a solid organ transplant from a transplant donor, the CMV-infected cells in most cases contain both infected cells of the patient origin and infected cells of the transplant donor origin. In specific embodiments when the human patient has been the recipient of a solid organ transplant, the population of allogeneic T cells that is administered to the human patient can share at least 2 (e.g., at least 2 out of 8) HLA alleles with all of the CMV-infected cells. In specific embodiments when the human patient has been the recipient of a solid organ transplant, the population of allogeneic T cells that is administered to the human patient can share at least 2 (e.g., at least 2 out of 8) HLA alleles with at least some of the CMV-infected cells. In some embodiments, a population of allogeneic T cells comprising CMV-specific T cells (or a T cell line from which to derive the population of allogeneic T cells) that shares at least 2 (e.g., at least 2 out of 8) HLA alleles with both the human patient and the transplant donor is selected for administering (the population of allogeneic T cells that is administered to the human patient then shares at least 2 (e.g., at least 2 out of 8) HLA alleles with all of the CMV-infected cells). In a specific embodiment when the human patient is at a high risk for organ allograft rejection, and CMV retinitis is the main problem without CMV viremia, a population of allogeneic T cells comprising CMV-specific T cells (or a T cell line from which to derive the population of allogeneic T cells) that shares at least 2 (e.g., at least 2 out of 8) HLA alleles with the human patient can be selected for administering (the population of allogeneic T cells that is administered to the human patient then shares at least 2 (e.g., at least 2 out of 8) HLA alleles with at least some of the CMV-infected cells). In a specific embodiment, (e.g., when the origin of the CMV-infected cells is determined to be the human patient only), a population of allogeneic T cells comprising CMV-specific T cells (or a T cell line from which to derive the population of allogeneic T cells) that shares at least 2 (e.g., at least 2 out of 8) HLA alleles with the human patient is selected for administering. In a specific embodiment (e.g., when the origin of the CMV-infected cells is determined to be the transplant donor only), a population of allogeneic T cells comprising CMV-specific T cells (or a T cell line from which to derive the population of allogeneic T cells) that shares at least 2 (e.g., at least 2 out of 8) HLA alleles with the transplant donor is selected for administering. In some embodiments when the patient has CMV-related viremia, a population of allogeneic T cells comprising CMV-specific T cells (or a T cell line from which to derive the population of allogeneic T cells) that shares at least 2 (e.g., at least 2 out of 8) HLA alleles with both the human patient and the transplant donor can be selected for administering. In certain embodiments, the methods further comprise prior to the administering step, a step of ascertaining the HLA assignment of the CMV-infected cells, the human patient, the transplant donor, or both the human patient and the transplant donor (as the case may be).

The HLA assignment (i.e., the HLA loci type) can be ascertained (i.e., typed) by any method known in the art. Non-limiting exemplary methods for ascertaining the HLA assignment can be found in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Hurley, "DNA-based typing of HLA for transplantation." in Leffell et al., eds., 1997, Handbook of Human Immunology, Boca Raton: CRC Press; Dunn, 2011, Int J Immunogenet 38:463-473; Erlich, 2012, Tissue Antigens, 80:1-11; Bontadini, 2012, Methods, 56:471-476; and Lange et al., 2014, BMC Genomics 15: 63.

In general, high-resolution typing is preferable for HLA typing. The high-resolution typing can be performed by any method known in the art, for example, as described in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Flomenberg et al., Blood, 104:1923-1930; Kögler et al., 2005, Bone Marrow Transplant, 36:1033-1041; Lee et al., 2007, Blood 110:4576-4583; Erlich, 2012, Tissue Antigens, 80:1-11; Lank et al., 2012, BMC Genomics 13:378; or Gabriel et al., 2014, Tissue Antigens, 83:65-75. In specific embodiments, the methods of treating CMV retinitis described herein further comprise prior to the administering step a step of ascertaining at least one HLA allele of the CMV-infected cells by high-resolution typing. In specific embodiments, the methods of treating CMV retinitis described herein further comprise prior to the administering step a step of ascertaining at least one HLA allele of the human patient by high-resolution typing. In specific embodiments when the human patient has been the recipient of a solid organ transplant from a transplant donor, the methods of treating CMV retinitis described herein further comprise prior to the administering step a step of ascertaining at least one HLA allele of the transplant donor by high-resolution typing. In specific embodiments, when the human patient has been the recipient of a solid organ transplant from a transplant donor, the methods of treating CMV retinitis described herein further comprise prior to the administering step a step of ascertaining at least one HLA allele of the human patient and at least one HLA allele of the transplant donor by high-resolution typing.

The HLA allele by which the population of allogeneic T cells is restricted can be determined by any method known in the art, for example, as described in Trivedi et al., 2005, Blood 105:2793-2801; Barker et al., 2010, Blood 116:5045-5049; Hasan et al., 2009, J Immunol, 183:2837-2850; or Doubrovina et al., 2012, Blood 120:1633-1646.

Preferably, the HLA allele by which the population of allogeneic T cells is restricted and is shared with at least some, optionally all, of the CMV-infected cells is defined by high-resolution typing. Preferably, the HLA alleles that are shared between the population of allogeneic T cells and at least some, optionally all, of the CMV-infected cells are defined by high-resolution typing. Most preferably, both the HLA allele by which the population of allogeneic T cells is restricted and is shared with at least some, and optionally all, of the CMV-infected cells, and the HLA alleles that are shared between the population of allogeneic T cells and at least some, optionally all, of the CMV-infected cells are defined by high-resolution typing.

5.2. Obtaining or Generating a Population of Allogeneic T Cells Comprising CMV-specific T Cells The population of allogeneic T cells comprising CMV-specific T cells that is administered to the human patient can be generated by a method known in the art, or can be selected from a preexisting bank (collection) of cryopreserved T cell lines (each T cell line comprising CMV-specific T cells) generated by a method known in the art, and thawed and preferably expanded prior to administration. Preferably, unique identifier for each T cell line in the bank is associated with information as to which HLA allele(s) the respective T cell line is restricted, the HLA assignment of the respective T cell line, and/or the anti-CMV cytotoxic activity of the respective T cell line measured by a method known in the art (for example, as described in Trivedi et al., 2005, Blood 105:2793-2801; or Hasan et al., 2009, J Immunol 183: 2837-2850). The population of allogeneic T cells and the T cell lines in the bank are preferably obtained or generated by methods described below.

In various embodiments, the methods of treating CMV retinitis further comprise prior to the administering step a step of obtaining the population of allogeneic T cells. Preferably, the population of allogeneic T cells comprising CMV-specific T cells are derived from CMV seropositive donors.

In specific embodiments, the step of obtaining the population of allogeneic T cells comprises fluorescence activated cell sorting for CMV-positive T cells from a population of blood cells. In a specific embodiment, the population of blood cells are peripheral blood mononuclear cells (PBMCs) isolated from a blood sample(s) obtained from a human donor. The fluorescence activated cell sorting can be performed by any method known in the art, which normally involves staining the population of blood cells with an antibody that recognizes at least one CMV antigen before the sorting step.

In specific embodiments, the step of obtaining the population of allogeneic T cells comprises generating the population of allogeneic T cells in vitro. The population of allogeneic T cells can be generated in vitro by any method known in the art. Non-limiting exemplary methods of generating the population of allogeneic T cells can be found in Trivedi et al., 2005, Blood 105:2793-2801; Hasan et al., 2009, J Immunol 183: 2837-2850; Koehne et al., 2015, Biol Blood Marrow Transplant S1083-8791(15)00372-9, published online May 29, 2015; O'Reilly et al., 2007, Immunol Res 38:237-250; and 0' Reilly et al., 2011, Best Practice & Research Clinical Haematology 24:381-391.

In certain embodiments, the step of generating the population of allogeneic T cells in vitro comprises sensitizing (i.e., stimulating) allogeneic T cells to one or more CMV antigens so as to produce CMV-specific T cells. In specific embodiments, the step of generating the population of allogeneic T cells in vitro comprises sensitizing allogeneic T cells to one or more CMV antigens presented by antigen presenting cells. The allogeneic T cells that are used for generating the population of allogeneic T cells in vitro can be isolated from the donor of the allogeneic T cells by any method known in the art, for example, as described in Trivedi et al., 2005, Blood 105:2793-2801; Hasan et al., 2009, J Immunol 183: 2837-2850; or O'Reilly et al., 2007, Immunol Res. 38:237-250. In a specific embodiment, the allogeneic T cells are enriched from peripheral blood lymphocytes separated from PBMCs of the donor of the allogeneic T cells. In a further specific embodiment, T cells are enriched from peripheral blood lymphocytes separated from PBMCs of the donor of the allogeneic T cells by depletion of adherent monocytes followed by depletion of natural killer cells. In various embodiments, the allogeneic T cells are cryopreserved for storage. In a specific embodiment, wherein the allogeneic T cells are cryopreserved, the cryopreserved allogeneic T cells are thawed and expanded in vitro before sensitizing. In a specific embodiment, wherein the allogeneic T cells are cryopreserved, the cryopreserved allogeneic T cells are thawed and then sensitized, but not expanded in vitro before sensitizing, and then optionally expanded. In specific embodiments, the allogeneic T cells are cryopreserved after sensitizing (sensitizing produces the CMV-specific T cells). In a specific embodiment, wherein the allogeneic T cells are cryopreserved after sensitizing, the cryopreserved allogeneic T cells are thawed and expanded in vitro to produce the population of allogeneic T cells comprising CMV-specific T cells. In another specific embodiment, wherein the allogeneic T cells are cryopreserved after sensitizing, the cryopreserved allogeneic T cells are thawed but not expanded in vitro to produce the population of allogeneic T cells comprising CMV-specific T cells. In other various embodiments, the allogeneic T cells are not cryopreserved. In a specific embodiment, wherein the allogeneic T cells are not cryopreserved, the allogeneic T cells are expanded in vitro before sensitizing. In a specific embodiment, wherein the allogeneic T cells are not cryopreserved, the allogeneic T cells are not expanded in vitro before sensitizing. In specific embodiments, the step of generating the population of allogeneic T cells in vitro further comprises, after sensitizing, cryopreserving the allogeneic T cells.

In specific embodiments, the methods of treating CMV retinitis described herein further comprise, before the administering step, steps of thawing cryopreserved CMV-antigen sensitized allogeneic T cells, and expanding the allogeneic T cells in vitro, to produce the population of allogeneic T cells.

In certain embodiments, the step of generating the population of allogeneic T cells in vitro comprises sensitizing allogeneic T cells using dendritic cells (preferably, the dendritic cells are derived from the donor of allogeneic T cells). In specific embodiments, the step of sensitizing allogeneic T cells using dendritic cells comprises loading the dendritic cells with at least one immunogenic peptide derived from one or more CMV antigens. In specific embodiments, the step of sensitizing allogeneic T cells using dendritic cells comprises loading the dendritic cells with a pool of overlapping peptides derived from one or more CMV antigens.

In certain embodiments, the step of generating the population of allogeneic T cells in vitro comprises sensitizing allogeneic T cells using cytokine-activated monocytes (preferably, the cytokine-activated monocytes are derived from the donor of allogeneic T cells). In specific embodiments, the step of sensitizing allogeneic T cells using cytokine-activated monocytes comprises loading the cytokine-activated monocytes with at least one immunogenic peptide derived from one or more CMV antigens. In specific embodiments, the step of sensitizing allogeneic T cells using cytokine-activated monocytes comprises loading the cytokine-activated monocytes with a pool of overlapping peptides derived from one or more CMV antigens.

In certain embodiments, the step of generating the population of allogeneic T cells in vitro comprises sensitizing allogeneic T cells using peripheral blood mononuclear cells (preferably, the peripheral blood mononuclear cells are derived from the donor of allogeneic T cells). In specific embodiments, the step of sensitizing allogeneic T cells using peripheral blood mononuclear cells comprises loading the peripheral blood mononuclear cells with at least one immunogenic peptide derived from one or more CMV antigens. In specific embodiments, the step of sensitizing allogeneic T cells using peripheral blood mononuclear cells comprises loading the peripheral blood mononuclear cells with a pool of overlapping peptides derived from one or more CMV antigens.

In certain embodiments, the step of generating the population of allogeneic T cells in vitro comprises sensitizing allogeneic T cells using an EBV-transformed B lymphocyte cell line (EBV-BLCL), for example, an EBV strain B95.8-transformed B lymphocyte cell line (preferably, the EBV-BLCL is derived from the donor of allogeneic T cells). The EBV-BLCL can be generated by any method known in the art, or as previously described in Trivedi et al., 2005, Blood 105:2793-2801 or Hasan et al., 2009, J Immunol 183:2837-2850. In specific embodiments, the step of sensitizing allogeneic T cells using an EBV-BLCL comprises loading the EBV-BLCL cells with at least one immunogenic peptide derived from one or more CMV antigens. In specific embodiments, the step of sensitizing allogeneic T cells using an EBV-BLCL comprises loading the EBV-BLCL cells with a pool of overlapping peptides derived from one or more CMV antigens.

In certain embodiments, the step of generating the population of allogeneic T cells in vitro comprises sensitizing allogeneic T cells using artificial antigen-presenting cells (AAPCs). In specific embodiments, the step of sensitizing allogeneic T cells using AAPCs comprises loading the AAPCs with at least one immunogenic peptide derived from one or more CMV antigens. In specific embodiments, the step of sensitizing allogeneic T cells using AAPCs comprises loading the AAPCs with a pool of overlapping peptides derived from one or more CMV antigens. In specific embodiments, the step of sensitizing allogeneic T cells using AAPCs comprises engineering the AAPCs to express at least one immunogenic CMV peptide or protein in the AAPCs.

In various embodiments, the pool of peptides is a pool of overlapping peptides spanning an antigen of CMV. In various embodiments, the pool of peptides is a pool of overlapping peptides spanning more than one antigen of CMV. In a specific embodiment, the pool of overlapping peptides is a pool of overlapping pentadecapeptides.

In specific embodiments, the population of allogeneic T cells has been cryopreserved for storage before administering. In specific embodiments, the population of allogeneic T cells has not been cryopreserved for storage before administering. In certain embodiments, the methods of treating CMV retinitis described herein further comprise, before the administering step, a step of thawing a cryopreserved form of the population of allogeneic T cells.

In various embodiments, the population of allogeneic T cells is derived from a T cell line. In specific embodiments, the T cell line has been cryopreserved for storage before administering. In specific embodiments, the T cell line has not been cryopreserved for storage before administering. In some embodiments, the T cell line has been expanded in vitro to derive the population of allogeneic T cells. In other embodiments, the T cell line has not been expanded in vitro to derive the population of allogeneic T cells. The T cell line can be sensitized to one or more CMV antigens (so as to produce CMV-specific T cells, for example, by a sensitizing step described above) before or after cryopreservation (if the T cell line has been cryopreserved), and before or after expanding in vitro (if the T cell line has been expanded in vitro). In certain embodiments, the methods of treating CMV retinitis described herein further comprise, before the administering step, a step of selecting the T cell line from a bank of a plurality of cryopreserved T cell lines (preferably each comprising CMV-specific T cells). Preferably, unique identifier for each T cell line in the bank is associated with information as to which HLA allele(s) the respective T cell line is restricted, and optionally also information as to the HLA assignment of the respective T cell line. In certain embodiments, the methods of treating CMV retinitis described herein further comprise, before the administering step, a step of thawing a cryopreserved form of the T cell line. In specific embodiments, the methods of treating CMV retinitis described herein further comprises, before the administering step, a step of expanding the T cell line (for example, after thawing a cryopreserved form of the T cell line) in vitro. The T cell line and the plurality of cryopreserved T cell lines can be generated by any method known in the art, for example, as described in Trivedi et al., 2005, Blood 105:2793-2801; Hasan et al., 2009, J Immunol 183: 2837-2850; Koehne et al., 2015, Biol Blood Marrow Transplant S1083-8791(15)00372-9, published online May 29, 2015; O'Reilly et al., 2007, Immunol Res 38:237-250; or O'Reilly et al., 2011, Best Practice & Research Clinical Haematology 24:381-391, or as describe above for generating the population of allogeneic T cells in vitro.

The population of allogeneic T cells comprising CMV-specific T cells that is administered to the human patient comprises CD8+ T cells, and in a specific embodiment also comprises CD4+ T cells.

The CMV-specific T cells administered in accordance with the methods described herein recognize at least one antigen of CMV. In specific embodiments, the CMV-specific T cells administered in accordance with the methods described herein recognize CMVpp65. In specific embodiments, the CMV-specific T cells administered in accordance with the methods described herein recognize CMV 1E1.

In specific embodiments, the population of allogeneic T cells has not been transduced ex vivo with a gene that encodes a CMV-specific T-cell receptor.

In specific embodiments, at least some, optionally all, of the cells of the population of allogeneic T cells are rapamycin-sensitive.

In specific embodiments, the population of allogeneic T cells is not administered in combination with a PD-1 antagonist.

5.3. Administration and Dosage

The route of administration of the population of allogeneic T cells and the amount to be administered to the human patient can be determined based on the condition of the human patient and the knowledge of the physician. Generally, the administration is intravenous.

In certain embodiments, the administering is by infusion of the population of allogeneic T cells. In some embodiments, the infusion is bolus intravenous infusion. In certain embodiments, the administering comprises administering at least about $1 \times 10^5$ T cells of the population of allogeneic T cells per kg per dose per week to the human patient. In some embodiments, the administering comprises administering about $1 \times 10^6$ to about $2 \times 10^6$ T cells of the population of allogeneic T cells per kg per dose per week to the human patient. In a specific embodiment, the administering comprises administering about $1 \times 10^6$ T cells of the population of allogeneic T cells per kg per dose per week to the human patient. In another specific embodiment, the administering comprises administering about $2 \times 10^6$ T cells of the population of allogeneic T cells per kg per dose per week to the human patient.

In certain embodiments, the methods of treating CMV retinitis described herein comprise administering at least 2 doses of the population of allogeneic T cells to the human patient. In specific embodiments, the methods of treating CMV retinitis described herein comprise administering 2, 3, 4, 5, or 6 doses of the population of allogeneic T cells to the human patient.

In certain embodiments, the methods of treating CMV retinitis described herein comprise administering a first cycle of one dose per week of the population of allogeneic T cells for 3 consecutive weeks followed by a washout period during which no dose of the population of allogeneic T cells is administered, followed by a second cycle of the one dose per week of the population of allogeneic T cells for 3 consecutive weeks. In certain embodiments, the methods of treating CMV retinitis described herein comprise administering at least two cycles of one dose per week of the population of allogeneic T cells for 3 consecutive weeks, each cycle separated by a washout period during which no dose of the population of allogeneic T cells is administered. In specific embodiments, the methods of treating CMV retinitis described herein comprise administering two, three, four, five, or six cycles of one dose per week of the population of allogeneic T cells for 3 consecutive weeks, each cycle separated by a washout period during which no dose of the population of allogeneic T cells is administered. In a specific embodiment, the washout period is about three weeks. Preferably, an additional cycle is administered only when the previous cycle has not exhibited toxicity (for example, no grade 3-5 serious adverse events, graded according to NCI CTCAE 4.0).

In a specific embodiment, the methods of treating CMV retinitis described herein comprises administering a first cycle of one dose per week of the population of allogeneic T cells for 3 consecutive weeks followed by a washout period during which no dose of the population of allogeneic T cells is administered, followed by a second cycle of one dose per week of the population of allogeneic T cells for 3 consecutive weeks, wherein each dose is about $1 \times 10^6$ T cells of the population of allogeneic T cells per kg, and the washout period is about three weeks.

In a specific embodiment, the methods of treating CMV retinitis described herein comprises administering about $1 \times 10^6$ T cells of the population of allogeneic T cells per kg per dose per week to the human patient for three consecutive weeks (i.e., 3 doses).

In certain embodiments, a first dosage regimen described herein is carried out for a first period of time, followed by a second and different dosage regimen described herein that is carried out for a second period of time, wherein the first period of time and the second period of time are optionally separated by a washout period (for example, about three weeks). Preferably, the second dosage regimen is carried out only when the first dosage regimen has not exhibited toxicity (for example, no grade 3-5 serious adverse events, graded according to NCI CTCAE 4.0).

The term "about" shall be construed so as to allow normal variation.

5.4. Serial Treatment with Different T Cell Populations

In certain embodiments, the methods of treating CMV retinitis further comprise, after administering to the human patient the population of allogeneic T cells, administering to the human patient a second population of allogeneic T cells comprising CMV-specific T cells; wherein the second population of allogeneic T cells is restricted by a different HLA allele shared with at least some, optionally all, of the CMV-infected cells. The second population of allogeneic T cells can be administered by any route and any dosage/administration regimen as described in Section 4.4. In a specific embodiment, the methods of treating CMV retinitis comprise administering a first cycle of one dose per week of the population of allogeneic T cells for 3 consecutive weeks followed by a washout period during which no dose of the population of allogeneic T cells is administered, followed by a second cycle of one dose per week of the second population of allogeneic T cells for 3 consecutive weeks. In a further specific embodiment, the washout period is about three weeks.

In certain embodiments, the human patient has no response, an incomplete response, or a suboptimal response (i.e., the human patient may still have a substantial benefit from continuing treatment, but has reduced chances of optimal long-term outcomes) after administering the population of allogeneic T cells and prior to administering the second population of allogeneic T cells.

In specific embodiments, two populations of allogeneic CMV-specific T cells that are each restricted by a different HLA allele shared with at least some, optionally all, of the CMV-infected cells are administered serially. In specific embodiments, three populations of allogeneic CMV-specific T cells that are each restricted by a different HLA allele shared with at least some, optionally all, of the CMV-infected cells are administered serially. In specific embodiments, four populations of allogeneic CMV-specific T cells that are each restricted by a different HLA allele shared with at least some, optionally all, of the CMV-infected cells are administered serially. In specific embodiments, more than four populations of allogeneic CMV-specific T cells that are each restricted by a different HLA allele shared with at least some, optionally all, of the CMV-infected cells are administered serially.

5.5. Combination Therapy

In various embodiments, the methods of treating CMV retinitis further comprise treating the human patient with an anti-viral compound to treat the CMV retinitis. In specific embodiments, the methods of treating CMV retinitis further comprise concurrently treating the human patient with an anti-viral compound to treat the CMV retinitis. In specific embodiments, the anti-viral compound is selected from the group consisting of ganciclovir, foscarnet, valganciclovir, cidofovir, leflunomide, and combinations thereof.

The anti-viral compound administered to the human patient may be administered to the human patient by a variety of routes. These include, but are not limited to, intravitreal, parenteral, intranasal, intratracheal, oral, intradermal, topical, intramuscular, intraperitoneal, transdermal, intravenous, infusion, intratumoral, conjunctival, subcutaneous, pulmonary, and any other local or systemic routes.

The amount of the anti-viral compound described herein or a pharmaceutical composition thereof which will be effective in the treatment of the CMV retinitis will depend on the nature of the disease and the condition of the patient, and can be determined by standard clinical techniques and the knowledge of the physician.

The precise dose and regime to be employed will also depend on the route of administration, the seriousness of the disease and each patient's circumstance and age, and should be decided according to the judgment of the physician.

When the anti-viral compound comprises ganciclovir, in specific embodiments, the ganciclovir can be administered as its sodium salt. In a specific embodiment, the ganciclovir is administered to the human patient intravenously (e.g., by constant-rate intravenous infusion) or intravitreally (e.g., by intravitreal injection). In a specific embodiment, the intravenous administration of ganciclovir (e.g., by constant-rate intravenous infusion) comprises administering ganciclovir at about 5 mg per kg per dose every 12 hours. In another specific embodiment, the intravenous administration of ganciclovir (e.g., by constant-rate intravenous infusion) comprises administering ganciclovir at about 5 mg per kg per dose per day. In another specific embodiment, the intravenous administration of ganciclovir (e.g., by constant-rate intravenous infusion) comprises administering ganciclovir at about 6 mg per kg per dose per day. In another specific embodiment, the intravenous administration of ganciclovir (e.g., by constant-rate intravenous infusion) comprises administering ganciclovir at about 2.5 mg per kg per dose every 12 hours. In another specific embodiment, the intravenous administration of ganciclovir (e.g., by constant-rate intravenous infusion) comprises administering ganciclovir at about 2.5 mg per kg per dose per day. In another specific embodiment, the intravenous administration of ganciclovir (e.g., by constant-rate intravenous infusion) comprises administering ganciclovir at about 1.25 mg per kg per dose per day. In another specific embodiment, the intravenous administration of ganciclovir (e.g., by constant-rate intravenous infusion) comprises administering ganciclovir at about 1.25 mg per kg per dose and 3 doses per week. In a specific embodiment, the intravenous administration of ganciclovir (e.g., by constant-rate intravenous infusion) comprises administering ganciclovir at about 5 mg per kg per dose every 12 hours for about 14 to 21 days, and then at about 5 mg per kg per dose per day and 7 days per week. In another specific embodiment, the intravenous administration of ganciclovir (e.g., by constant-rate intravenous infusion) comprises administering ganciclovir at about 5 mg per kg per dose every 12 hours for about 14 to 21 days, and then at about 6 mg per kg per dose per day and 5 days per week. In a specific embodiment, the intravitreal administration of ganciclovir (e.g., by intravitreal injection) comprises administering ganciclovir at about 2 mg to 5 mg per dose (e.g., in a volume of 0.1 mL). In another specific embodiment, the intravitreal administration of ganciclovir (e.g., by intravitreal injection) comprises administering ganciclovir at about 2 mg per dose (e.g., in a volume of 0.1 mL). In another specific embodiment, the intravitreal administration of ganciclovir (e.g., by intravitreal injection) comprises administering ganciclovir at about 3 mg per dose (e.g., in a volume of 0.1 mL). In another specific embodiment, the intravitreal administration of ganciclovir (e.g., by intravitreal injection) comprises administering ganciclovir at about 4 mg per dose (e.g., in a volume of 0.1 mL). In another specific embodiment, the intravitreal administration of ganciclovir (e.g., by intravitreal injection) comprises administering ganciclovir at about 5 mg per dose (e.g., in a volume of 0.1 mL). The frequency of intravitreal administration (e.g., by intravitreal injection) of ganciclovir can be determined by the location, severity, and response of the disease, and tolerance of the human patient to the ganciclovir treatment, and can range from, for example, every other day to biweekly. In a specific embodiment, the intravitreal administration of ganciclovir (e.g., by intravitreal injection) comprises administering ganciclovir biweekly. In another specific embodiment, the intravitreal administration of ganciclovir (e.g., by intravitreal injection) comprises administering ganciclovir weekly. In another specific embodiment, the intravitreal administration of ganciclovir (e.g., by intravitreal injection) comprises administering ganciclovir every other day. When the human patient has an initial presentation of CMV retinitis and/or is in a vision threatening situation (e.g., optic nerve and/or macula threatening), in a specific embodiment, the intravitreal administration of ganciclovir (e.g., by intravitreal injection) comprises administering ganciclovir biweekly. Intravitreal administration (e.g., by intravitreal injection) of ganciclovir may or may not be performed in conjunction with systemic therapy with ganciclovir or other anti-viral compounds. Intravitreal administration (e.g., by intravitreal injection) of ganciclovir may or may not be performed in conjunction with intravitreal administration (e.g., by intravitreal injection) of other anti-viral compounds. The precise dose of ganciclovir and regime to be employed can also be adjusted depending on the route of administration, the seriousness of the disease and the patient's circumstance and age, and can be decided according to the judgment of the physician.

When the anti-viral compound comprises valganciclovir, in specific embodiments, the valganciclovir can be administered as valganciclovir hydrochloride. In a specific embodiment, the valganciclovir is administered to the human patient orally (e.g., in the form of a tablet or oral solution). In a specific embodiment, the oral administration of valganciclovir (e.g., in the form of a tablet or oral solution) comprises administering valganciclovir at about 900 mg per dose and two doses per day. In another specific embodiment, the oral administration of valganciclovir (e.g., in the form of a tablet or oral solution) comprises administering valganciclovir at about 900 mg per dose per day. In another specific embodiment, the oral administration of valganciclovir (e.g., in the form of a tablet or oral solution) comprises administering valganciclovir at about 450 mg per dose and two doses per day. In another specific embodiment, the oral administration of valganciclovir (e.g., in the form of a tablet or oral solution) comprises administering valganciclovir at about 450 mg per dose per day. In another specific embodiment, the oral administration of valganciclovir (e.g., in the form of a tablet or oral solution) comprises administering valganciclovir at about 450 mg per dose and one dose every two days. In another specific embodiment, the oral administration of valganciclovir (e.g., in the form of a tablet or oral solution) comprises administering valganciclovir at about 450 mg per dose and two doses every week. In a specific embodiment, the oral administration of valganciclovir (e.g., in the form of a tablet or oral solution) comprises administering valganciclovir at about 900 mg per dose and two doses per day for 21 days, and then at about 900 mg per dose per day. When the human patient is an adult patient who has received a heart or kidney-pancreas transplant, in a specific embodiment, the oral administration of valganciclovir (e.g., in the form of a tablet or oral solution) comprises administering valganciclovir at about 900 mg per dose per day starting within 10 days of transplantation until about 100 days post-transplantation. When the human patient is an adult patient who has received a kidney transplant, in a specific embodiment, the oral administration of valganciclovir (e.g., in the form of a tablet or oral solution) comprises administering valganciclovir at about 900 mg per dose per day starting within 10 days of transplantation until about 200 days post-transplantation. The precise dose of valganciclovir and regime to be employed can also be adjusted depending on the route of administration, the seriousness of the disease and the patient's circumstance and age, and can be decided according to the judgment of the physician.

When the anti-viral compound comprises foscarnet, in specific embodiments, the foscarnet can be administered as its sodium salt. In a specific embodiment, the foscarnet is administered to the human patient intravenously (e.g., by controlled intravenous infusion) or intravitreally (e.g., by intravitreal injection). In a specific embodiment, the intravenous administration of foscarnet (e.g., by controlled intravenous infusion) comprises administering foscarnet at about 90 mg per kg per dose every 12 hours. In another specific embodiment, the intravenous administration of foscarnet (e.g., by controlled intravenous infusion) comprises administering foscarnet at about 60 mg per kg per dose every 8 hours. In another specific embodiment, the intravenous administration of foscarnet (e.g., by controlled intravenous infusion) comprises administering foscarnet at about 90 mg per kg per dose per day. In another specific embodiment, the intravenous administration of foscarnet (e.g., by controlled intravenous infusion) comprises administering foscarnet at about 120 mg per kg per dose per day. In a specific embodiment, the intravenous administration of foscarnet (e.g., by controlled intravenous infusion) comprises administering foscarnet at about 90 mg per kg per dose every 12 hours or at about 60 mg per kg per dose every 8 hours for about 2 to 3 weeks, and then at about 90 mg per kg per dose per day. In another specific embodiment, the intravenous administration of foscarnet (e.g., by controlled intravenous infusion) comprises administering foscarnet at about 90 mg per kg per dose every 12 hours or at about 60 mg per kg per dose every 8 hours for about 2 to 3 weeks, and then at about 120 mg per kg per dose per day. In a specific embodiment, the intravitreal administration of foscarnet (e.g., by intravitreal injection) comprises administering foscarnet at about 2.4 mg per dose (e.g., in a volume of 0.1 mL). The frequency of intravitreal administration (e.g., by intravitreal injection) of foscarnet can be determined by the location, severity, and response of the disease, and tolerance of the human patient to the foscarnet treatment, and can range from, for example, every other day to biweekly. In a specific embodiment, the intravitreal administration of foscarnet (e.g., by intravitreal injection) comprises administering foscarnet biweekly. In another specific embodiment, the intravitreal administration of foscarnet (e.g., by intravitreal injection) comprises administering foscarnet weekly. In another specific embodiment, the intravitreal administration of foscarnet (e.g., by intravitreal injection) comprises administering foscarnet every other day. When the human patient has an initial presentation of CMV retinitis and/or is in a vision threatening situation (e.g., optic nerve and/or macula threatening), in a specific embodiment, the intravitreal administration of foscarnet (e.g., by intravitreal injection) comprises administering foscarnet biweekly. Intravitreal administration (e.g., by intravitreal injection) of foscarnet may or may not be performed in conjunction with systemic therapy with foscarnet or other anti-viral compounds. Intravitreal administration (e.g., by intravitreal injection) of foscarnet may or may not be performed in conjunction with intravitreal administration (e.g., by intravitreal injection) of other anti-viral compounds. The precise dose of foscarnet and regime to be employed can also be adjusted depending on the route of administration, the seriousness of the disease and the patient's circumstance and age, and can be decided according to the judgment of the physician.

When the anti-viral compound comprises cidofovir, in specific embodiments, the cidofovir is administered to the human patient intravenously (e.g., by infusion). In a specific embodiment, the intravenous administration of cidofovir (e.g., by infusion) comprises administering cidofovir at about 5 mg per kg per dose per week. In another specific embodiment, the intravenous administration of cidofovir (e.g., by infusion) comprises administering cidofovir at about 5 mg per kg per dose and one dose every 2 weeks. In a specific embodiment, the intravenous administration of cidofovir (e.g., by infusion) comprises administering cidofovir at about 5 mg per kg per dose per week for about 2 weeks, and then at about 5 mg per kg per dose and one dose every 2 weeks. The precise dose of cidofovir and regime to be employed can also be adjusted depending on the route of administration, the seriousness of the disease and the patient's circumstance and age, and can be decided according to the judgment of the physician.

When the anti-viral compound comprises leflunomide, in specific embodiments, the leflunomide is administered to the human patient orally (e.g., in the form of a tablet). In a specific embodiment, the oral administration of leflunomide (e.g., in the form of a tablet) comprises administering leflunomide at about 100 mg per dose per day. In another specific embodiment, the oral administration of leflunomide (e.g., in the form of a tablet) comprises administering leflunomide at about 20 mg per dose per day. In another specific embodiment, the oral administration of leflunomide (e.g., in the form of a tablet) comprises administering leflunomide at about 10 mg per dose per day. In a specific embodiment, the oral administration of leflunomide (e.g., in the form of a tablet) comprises administering leflunomide at about 100 mg per dose per day for 3 days, and then at about 20 mg per dose per day. In another specific embodiment, the oral administration of leflunomide (e.g., in the form of a tablet) comprises administering leflunomide at about 100 mg per dose per day for 3 days, and then at about 10 mg per dose per day. The precise dose of leflunomide and regime to be employed can also be adjusted depending on the route of administration, the seriousness of the disease and the patient's circumstance and age, and can be decided according to the judgment of the physician.

In embodiments wherein the human patient is treated with both a population of allogeneic T cells comprising CMV-specific T cells and an anti-viral compound as described herein, the population of allogeneic T cells comprising CMV-specific T cells and the antiviral compound can be administered to the human patient concurrently, for example, at about the same time, at the same day, or same week, or same multi-week period during which the population of allogeneic T cells is administered weekly, or on similar dosing schedules, or on different but overlapping dosing schedules.

In specific embodiments, the anti-viral compound can be administered before (e.g., about 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months or 8 months before) or after (e.g., about 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months or 8 months after) the administration of the population of allogeneic T cells comprising CMV-specific T cells.

The term "about" shall be construed so as to allow normal variation.

5.6. Patients

The human patient can be anyone who has CMV retinitis (e.g., diagnosed by ophthalmologic examination) and who is infected with HIV or has been the recipient of a solid organ transplant. In specific embodiments, the human patient has an active, not latent, CMV infection.

In specific embodiments, a CMV in the human patient has at least one mutation in its genome that confers resistance to one or more anti-viral agents. In a specific embodiment, the one or more anti-viral agents are selected from the group consisting of ganciclovir, foscarnet, valganciclovir, cidofovir, leflunomide, and combinations thereof. In a specific embodiment, the mutation is in the UL97 (cytomegalovirus viral phosphotransferase) gene. In a further specific embodiment, the mutation in the UL97 gene confers resistance to ganciclovir and valganciclovir. In another specific embodiment, the mutation is in the UL54 (cytomegalovirus DNA polymerase) gene. In another further specific embodiment, the mutation in the UL54 gene confers resistance to foscarnet and cidofovir. In another further specific embodiment, the mutation in the UL54 gene confers resistance to ganciclovir, valganciclovir, foscarnet and cidofovir. In another specific embodiment, a first mutation is in the UL97 gene and a second mutation is in the UL54 gene. In another further specific embodiment, a first mutation is in the UL97 gene and a second mutation is in the UL54 gene, wherein the first mutation in the UL97 gene confers resistance to ganciclovir and valganciclovir, and the second mutation in the UL54 gene confers resistance to foscarnet and cidofovir. In another further specific embodiment, a first mutation is in the UL97 gene and a second mutation is in the UL54 gene, wherein the first mutation in the UL97 gene confers resistance to ganciclovir and valganciclovir, and the second mutation in the UL54 gene confers resistance to ganciclovir, valganciclovir, foscarnet and cidofovir.

In certain embodiments, the methods of treating CMV retinitis further comprise prior to said administering step a step of genotyping a CMV of the human patient. In specific embodiments, the methods of treating CMV retinitis further comprise genotyping a CMV of the human patient to identify at least one mutation (e.g., mutation(s) in the UL97 gene and/or mutation(s) in the UL54 gene) that confers resistance to one or more anti-viral agents, before the administering of the population of allogeneic T cells comprising CMV-specific T cells. CMV can be genotyped by any method known in the art, for example, by PCR or DNA sequencing, and can use any infected cell or tissue sample from the patient (e.g., a cell/tissue sample from the eye or blood). The genotyping can be performed using any commercially available kit for genotyping CMV or in any clinical reference laboratory.

CMV retinitis is an inflammation of the retina caused by human cytomegalovirus, which leads to progressive loss of vision and blindness, and usually occurs in immunocompromised patients.

In specific embodiments, the human patient has completely lost his/her vision. In specific embodiments, the human patient has lost more than 90%, 80%, 70%, 60%, 50%, 40%, 30%, 20%, or 10% of his/her vision. In specific embodiments, the human patient has lost about 90%, 80%, 70%, 60%, 50%, 40%, 30%, 20%, or 10% of his/her vision. In specific embodiments, the human patient has improved vision (for example, by about 10%, 20%, 30%, 40%, 50%, 60%, 70%, 80%, 90%, 100%, 150%, 200%, 250%, 300%, 400% or 500%, or by more than 10%, 20%, 30%, 40%, 50%, 60%, 70%, 80%, 90%, 100%, 150%, 200%, 250%, 300%, 400% or 500%) after being administered the population of allogeneic T cells comprising CMV-specific T cells. In specific embodiments, the human patient has stabilized vision after being administered the population of allogeneic T cells comprising CMV-specific T cells. In specific embodiments, the human patient has complete resolution of retinal inflammation after administered the population of allogeneic T cells comprising CMV-specific T cells. In specific embodiments, the human patient has partial resolution of retinal inflammation after administered the population of allogeneic T cells comprising CMV-specific T cells.

In alternative embodiments, the human patient is infected with HIV, or has been the recipient of a solid organ transplant from a transplant donor.

In certain embodiments, the human patient is infected with HIV. In specific embodiments, the human patient has AIDS. In a specific embodiment, the human patient is an AIDS patient with mid to higher level viral loads. In specific embodiments, the human patient does not develop uveitis after administration of the population of allogeneic T cells comprising CMV-specific T cells.

In certain embodiments, the human patient has been the recipient of a solid organ transplant from a transplant donor. In specific embodiments, the solid organ transplant that the human patient has received is a kidney transplant, a liver transplant, a heart transplant, an intestinal transplant, a pancreas transplant, a lung transplant, a small bowel transplant, or a combination thereof. In a specific embodiment, the solid organ transplant that the human patient has received is a kidney transplant. In specific embodiments wherein the human patient has been the recipient of a solid organ transplant from a transplant donor, the population of allogeneic T cells is derived from a donor other than the transplant donor. In specific embodiments, the human patient does not develop uveitis after administration of the population of allogeneic T cells comprising CMV-specific T cells. In specific embodiments, the human patient does not develop organ allograft rejection after administration of the population of allogeneic T cells comprising CMV-specific T cells.

In specific embodiments, the human patient has not been the recipient of a hematopoietic stem cell transplant (e.g., a bone marrow transplant, a peripheral blood stem cell transplant, or a cord blood transplant).

In specific embodiments, the human patient has failed a previous therapy to treat the CMV retinitis. A human patient is considered to have failed a therapy to treat the CMV retinitis if the CMV retinitis is resistant to the therapy and/or if the human patient has been taken off the therapy due to intolerance of the therapy (for example, due to toxicity of the therapy in view of the patient's age or condition). CMV retinitis is considered resistant to a therapy, if the CMV retinitis has no response, or has an incomplete response (a response that is less than a complete remission), or progresses, or relapses after the therapy. A complete remission is a complete resolution of all clinical evidence of the disease, optionally confirmed by ophthalmologic examination, lasting, for example, for at least three weeks following completion of the therapy. In specific embodiments, the previous therapy is treatment with at least one anti-viral agent. In a specific embodiment, the at least one anti-viral agent is selected from the group consisting of ganciclovir, foscarnet, valganciclovir, cidofovir, leflunomide, and combinations thereof. In a specific embodiment, the at least one anti-viral agent has been administered systematically. In a specific embodiment, the at least one anti-viral agent has been administered locally to the eye. In specific embodiments, the previous therapy is a therapy to recover or increase the immune function of the human patient.

6. EXAMPLE

Certain embodiments provided herein are illustrated by the following non-limiting example, which demonstrates that the therapy with a population of allogeneic T cells comprising CMV-specific T cells according to the invention is effective in treating CMV retinitis in a human patient who is infected with HIV or who has been the recipient of a solid organ transplant.

6.1. Introduction

Although it is reassuring that intravenously infused donor derived T cells can cross the blood brain barrier and enter the CNS, it could not be assumed from prior studies that the T-cells would cross the blood-retina barrier for effective treatment of CMV retinitis. Assuming that T-cells would enter the retina, a further concern for treatment of retinitis with adoptively transferred T-cells would be the potential for inducing immune recovery uveitis, which is an entity well described in AIDS patients with CMV retinitis treated with HAART, who develop uveitis upon recovery of immune function (Jabs et al., 2015, Ophthalmology pii:S0161-6420 (15)00175-X, published online Apr. 16, 2015). The use of third party CMV-specific T-cells for the treatment of retinitis raises additional concerns about appropriate homing of the infused T-cells to the eye, and of additional potential risks with respect to inducing uveitis.

The development of retinitis and corresponding immune control of infection have thus far not been perfectly correlated. For example, paradoxically, active HCMV retinitis has been reported in the presence of persistently high CD4+ T-cell counts during HAART. Although this might be explained by the low number of circulating HCMV-specific CD8+ T cells, it has not been clearly shown (Lin et al., 2002, Retina 22:268-277). The study described herein and recent observations by others provide evidence that CMV viral load during retinitis does not necessarily correlate with disease progression, which is in contrast to other HCMV diseases, such as pneumonitis or colitis. Furthermore, several reports in HIV patients have shown that, in some cases, the restoration of immune activity by antiretroviral (HAART) therapy might be associated with the development of retinitis. In such cases, the presumption would be that the retina was latently infected with CMV throughout, but became inflamed with the infiltration of immune cells after HAART.

6.2. Methods:

All cellular products were processed in the GMP facility at Memorial Sloan Kettering Cancer Center under standard SOPs and FDA compliant protocols.

The generation and characterization of CMVpp65 epitope specific T-cells has been detailed in the recently published manuscript (Koehne et al., 2015, Biol Blood Marrow Transplant pii: S1083-8791(15)00372-9, published online May 29, 2015). CMVpp65 specific T-cells were generated from CMV-seropositive healthy marrow transplant donors by sensitization in vitro with autologous, cytokine-activated monocytes (CAMS) loaded with a pool of synthetic 15-mer peptides spanning the sequence of CMV protein pp65. Autologous transplant donor-derived CAMS and Epstein-Barr virus transformed B lymphocyte cell lines (EBV-BLCLs) were generated as previously described (Trivedi et al., 2005, Blood 105:2793-2801; Hasan et al., 2009, J Immunol 183:2837-2850).

Figure 1:
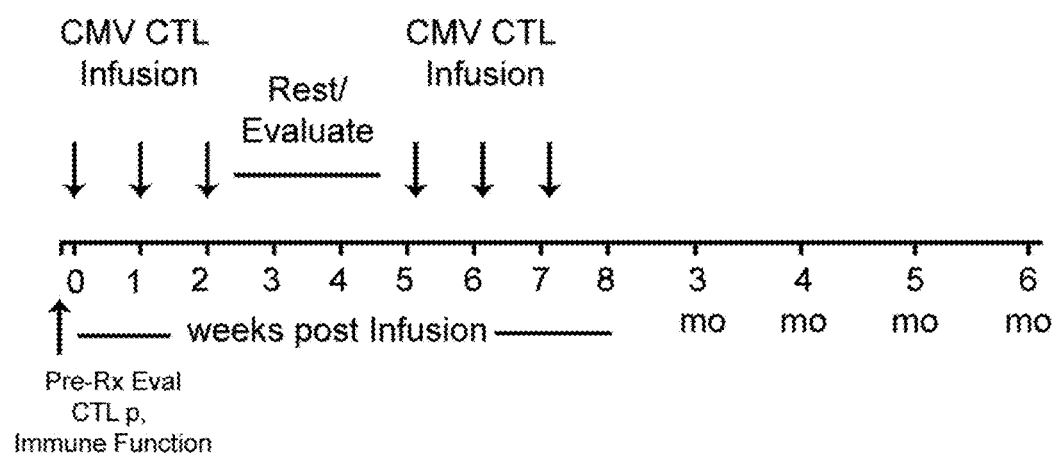
FIG. 1 depicts the schema of treating CMV retinitis using CMV-specific T cells.

CMV-specific T cells were infused as per the clinical protocol according to the treatment schema outlined in FIG. 1. T cells were chosen from a GMP grade T cell bank from donors who had consented to the third party use of their T-cells. T-cells matching the patient for at least 2 HLA alleles that demonstrated anti-CMV cytotoxic activity restricted by an HLA allele shared with the patient were selected for infusion. Initial treatment consisted of 3 weekly infusions of $1 \times 10^6$ T-cells/kg. This was followed by an observation period of 3 weeks, after which patients could receive another cycle of 3 weekly infusions based on response. As shown in FIG. 2, patients received 1-3 cycles of CMV-specific T-cells, that were appropriately matched for 2 or more HLA alleles and appropriately restricted for CMV activity. Blood samples from patients were monitored at specific intervals post infusion for immune function as well as detection of CMV-specific T-cells.

6.3. Results:

Immunosuppressed patients developing progressive retinitis despite treatment with antiviral drugs are in imminent danger of losing vision very quickly. Banked third party donor derived CMV-specific T-cells constitutes an immediately available therapy for such patients. Six patients with clinically documented CMV retinitis were treated using adoptively transferred third party donor derived CMV-specific T-cells comprising cytotoxic T cells (CTLs) under an IRB (Institutional Review Board) approved protocol. Four of these patients were BMT recipients, one was a kidney transplant recipient, and one was an HIV-positive patient.

Figure 3:
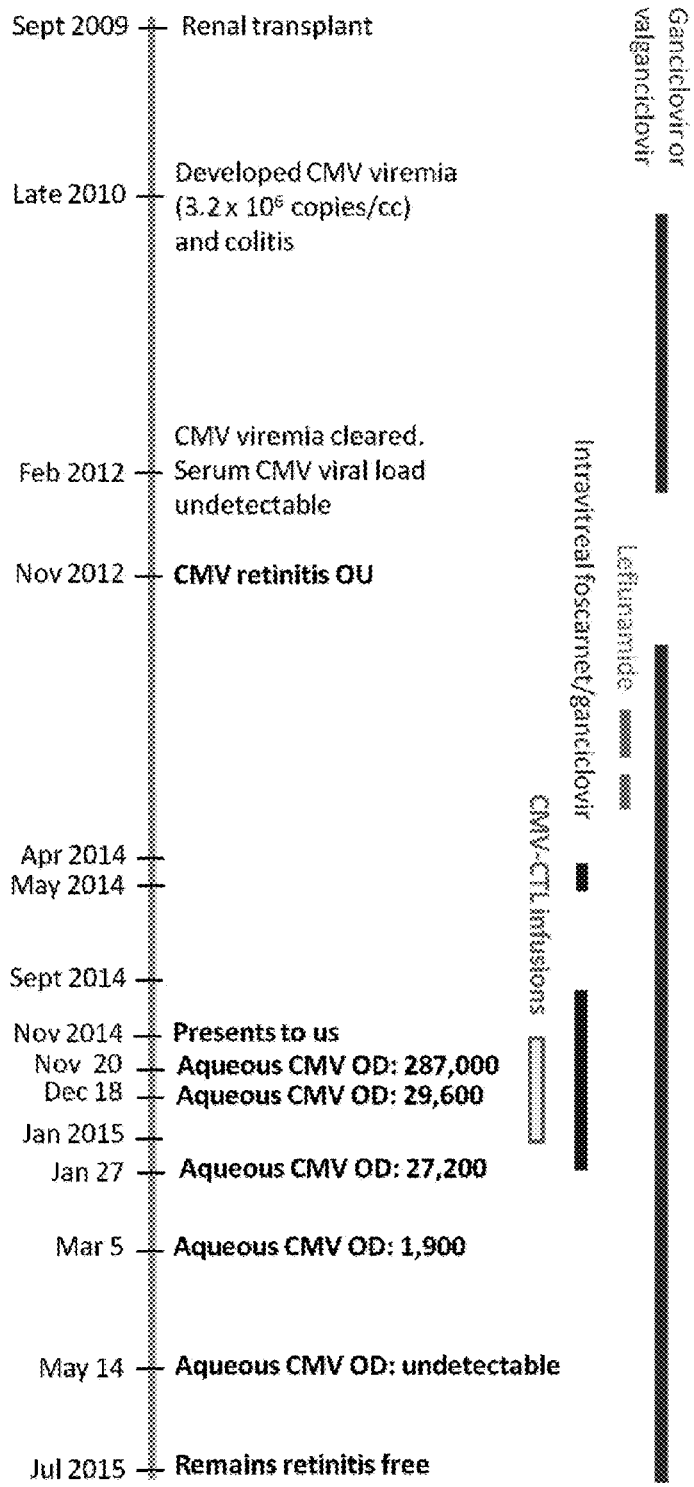
FIG. 3 depicts the clinical chronology of patient #5. CMV viral titer is presented in international units per ml (IU/ml) (1 IU=0.53 copies of CMV).

Patient #5 (see clinical chronology of FIG. 3) is a 68-year-old male who received a kidney transplant, and developed CMV retinitis. He had a history of Wegener's granulomatosis nephropathy status post kidney transplant, and was on chronic immunosuppressive therapy (prednisone, tacrolimus, and mycophenolate) for graft rejection prophylaxis. His ophthalmologic course was also complicated by glaucoma requiring tube shunt OD (oculus dexter, i.e., right eye), tube shunt revision/CE/IOL (cataract extraction with intraocular lens implant) OD, tube shunt/CE/IOL OS (oculus sinister, i.e., left eye), 2nd tube shunt surgery OS, diode laser cyclophotocoagulation OD. The patient could not tolerate aggressive systemic antiviral therapy due to kidney toxicity of those agents (foscarnet and ganciclovir), and therefore was treated with intravitreal injections of ganciclovir and foscarnet, and leflunamide, but the patient did not respond. The patient was also treated with valganciclovir. In addition, he developed peripheral neuropathy due to a side effect of leflunomide. It was found that the CMV of this patient had a mutation in UL97, conferring resistance to ganciclovir and valganciclovir. He was therefore referred for CMV specific T-cell therapy. The patient received two cycles of CMV specific T cells for a total of 6 doses of T cells. Fluid was aspirated from his eye during treatment, and demonstrated complete clearance of virus from the eye (FIG. 4, Table 1).

Patient #6 is a 56-year-old male with HIV infection and CMV retinitis. The patient progressed after treatment with systemic antivirals followed by biweekly, and then weekly injections of antivirals in the eye for 2-3 months. The patient received injections of antivirals in the eye twice a week, and became intolerant of these frequent injections. He was therefore referred for CMV specific T-cell therapy. This patient received one cycle of CMV specific T cells for a total of 3 doses of T cells and had a complete clearance of retinal disease (Table 1).

of a pre-existing epiretinal membrane (macular pucker), not secondary to the T cell therapy or CMV retinitis activation.

CMV-specific T-cells were enumerated from the patients at different time points post infusion. An expansion in the numbers of CMV-specific T-cells could be demonstrated in all responding patients, including the patient with a partial response. As shown in FIG. 5 for a representative example (patient #5), increases in CMV-specific T cells were associated with decline in CMV viral load in blood. In the HIV-positive patient, functional CMV-specific T-cells were able to be detected for 6 weeks post infusion of the last dose of T-cells.

7. INCORPORATION BY REFERENCE

Various publications are cited herein, the disclosures of which are hereby incorporated by reference herein in their entireties.

What is claimed is:

1. A method of treating CMV (cytomegalovirus) retinitis in a human patient in need thereof, comprising administering to the human patient a population of allogeneic T cells comprising CMV-specific T cells; wherein the human patient is infected with HIV, wherein the CMV-specific T cells recognize CMVpp65, and wherein the population of allogeneic T cells is restricted by an HLA allele shared with at least some, optionally all, of the CMV-infected cells.

TABLE 1

Patient #5 and patient #6.

| Patient | Age (yr) | Underlying Medical Diagnosis | # Rounds T-cell Infusions | VA Pre-T-cells | Final VA | F/u (mth) | Recurrent Retinitis | Uveitic Episodes | Retinal detachment |
|---|---|---|---|---|---|---|---|---|---|
| #5 | 68 | Renal transplant on immunosuppressants for graft rejection prophylaxis | 2 | CF OD | 3/200 OD | 8 | None | None | None |
| #6 | 56 | HIV with chronically suppressed CD4 count <50 despite HAART; history of lymphoma s/p chemo | 1 | 20/25 OD | 20/20 | 14 | None | Cystoid macular edema OD 7 months after infusions (no retinitis, CMV PCR negative, self-resolved) | None |

VA: visual acuity.
CF: count fingers (worse than 20/400).
F/u: follow up.
mth: month.
s/p: status post.
OD: oculus dexter, i.e., right eye.

Four of the 6 treated patients, including the one HIV-positive patient and the one kidney transplant recipient, had a complete response to treatment with complete resolution of retinal inflammation on ophthalmologic examination. The vision improved in these patients, or stabilized. One BMT patient had a partial response to treatment. He received 2 cycles of treatment after which the response was sustained with no deterioration. One BMT patient received only one dose of CMV-specific T cells and could not continue, and is therefore not evaluable.

No GvHD was observed in any of the treated patients. Patient #5 has not demonstrated any evidence of uveitis. The patient with HIV (#6) had a complete response to treatment. This patient transiently developed vitreal inflammation which resolved without sequelae and with complete resolution of CMV retinitis. The cystoid macular edema that developed in patient #6 was apparently due to a worsening 2. A method of treating CMV retinitis in a human patient in need thereof, comprising administering to the human patient a population of allogeneic T cells comprising CMV-specific T cells; wherein the human patient has been the recipient of a solid organ transplant from a transplant donor, wherein the CMV-specific T cells recognize CMVpp65, and wherein the population of allogeneic T cells is restricted by an HLA allele shared with at least some, optionally all, of the CMV-infected cells.

3. The method of claim 2, wherein the solid organ transplant is a kidney transplant, a liver transplant, a heart transplant, an intestinal transplant, a pancreas transplant, a lung transplant, a small bowel transplant, or a combination thereof.

4. The method of claim 1, which further comprises prior to said administering step a step of generating the population of allogeneic T cells in vitro.

5. The method of claim 4, wherein the step of generating the population of allogeneic T cells in vitro comprises sensitizing allogeneic T cells to CMVpp65.

6. The method of claim 1, wherein the administering is by infusion of the population of allogeneic T cells.

7. The method of claim 1, further comprising, after administering to the human patient the population of allogeneic T cells, administering to the human patient a second population of allogeneic T cells comprising CMV-specific T cells that recognize CMVpp65; wherein the second population of allogeneic T cells is restricted by a different HLA allele shared with at least some, optionally all, of the CMV-infected cells.

8. The method of claim 1, wherein the human patient has failed a previous therapy to treat the CMV retinitis.

9. The method of claim 8, wherein the previous therapy is treatment with at least one anti-viral agent.

10. The method of claim 9, wherein the at least one anti-viral agent is selected from the group consisting of ganciclovir, foscarnet, valganciclovir, cidofovir, leflunomide, and combinations thereof.

11. The method of claim 1, wherein the population of allogeneic T cells has not been transduced ex vivo with a gene that encodes a CMV-specific T-cell receptor.

12. The method of claim 1, wherein at least some, optionally all, of the cells of the population of allogeneic T cells are rapamycin-sensitive.

13. The method of claim 1, wherein the population of allogeneic T cells is not administered in combination with a PD-1 antagonist.

14. The method of claim 1, wherein the human patient has not been the recipient of a hematopoietic stem cell transplant.

15. The method of claim 1, wherein the human patient has an active, not latent, CMV infection.

16. The method of claim 1, wherein a CMV in the human patient has at least one mutation in its genome that confers resistance to one or more anti-viral agents.

17. The method of claim 16, wherein the one or more anti-viral agents are selected from the group consisting of ganciclovir, foscarnet, valganciclovir, cidofovir, leflunomide, and combinations thereof.

18. The method of claim 16, wherein the at least one mutation is a mutation in the UL97 gene, a mutation in the UL54 gene, or a first mutation in the UL97 gene and a second mutation in the UL54 gene.

19. The method of claim 16, which further comprises prior to said administering step a step of genotyping a CMV of the human patient.

20. The method of claim 2, wherein the population of allogeneic T cells has not been transduced ex vivo with a gene that encodes a CMV-specific T-cell receptor.

21. The method of claim 2, wherein at least some, optionally all, of the cells of the population of allogeneic T cells are rapamycin-sensitive.

22. The method of claim 2, wherein the population of allogeneic T cells is not administered in combination with a PD-1 antagonist.

23. The method of claim 2, wherein the human patient has not been the recipient of a hematopoietic stem cell transplant.

24. The method of claim 2, wherein the human patient has an active, not latent, CMV infection.

25. The method of claim 1, wherein the administering is by intravenous infusion of the population of allogeneic T cells.

26. The method of claim 2, wherein the administering is by intravenous infusion of the population of allogeneic T cells.

27. The method of claim 11, wherein the administering is by intravenous infusion of the population of allogeneic T cells.

28. The method of claim 12, wherein the administering is by intravenous infusion of the population of allogeneic T cells.

29. The method of claim 13, wherein the administering is by intravenous infusion of the population of allogeneic T cells.

30. The method of claim 14, wherein the administering is by intravenous infusion of the population of allogeneic T cells.

31. The method of claim 15, wherein the administering is by intravenous infusion of the population of allogeneic T cells.

32. The method of claim 20, wherein the administering is by intravenous infusion of the population of allogeneic T cells.

33. The method of claim 21, wherein the administering is by intravenous infusion of the population of allogeneic T cells.

34. The method of claim 22, wherein the administering is by intravenous infusion of the population of allogeneic T cells.

35. The method of claim 23, wherein the administering is by intravenous infusion of the population of allogeneic T cells.

36. The method of claim 24, wherein the administering is by intravenous infusion of the population of allogeneic T cells.

37. The method of claim 1, wherein: (a) the population of allogeneic T cells has not been transduced ex vivo with a gene that encodes a CMV-specific T-cell receptor; (b) at least some, optionally all, of the cells of the population of allogeneic T cells are rapamycin-sensitive; (c) the population of allogeneic T cells is not administered in combination with a PD-1 antagonist; (d) the human patient has not been the recipient of a hematopoietic stem cell transplant; (e) the human patient has an active, not latent, CMV infection; and (f) the administering is by intravenous infusion of the population of allogeneic T cells.

38. The method of claim 2, wherein: (a) the population of allogeneic T cells has not been transduced ex vivo with a gene that encodes a CMV-specific T-cell receptor; (b) at least some, optionally all, of the cells of the population of allogeneic T cells are rapamycin-sensitive; (c) the population of allogeneic T cells is not administered in combination with a PD-1 antagonist; (d) the human patient has not been the recipient of a hematopoietic stem cell transplant; (e) the human patient has an active, not latent, CMV infection; and (f) the administering is by intravenous infusion of the population of allogeneic T cells.

39. The method of claim 8, wherein the CMV retinitis is resistant to the previous therapy.

40. The method of claim 39, wherein the previous therapy is treatment with at least one anti-viral agent.

41. The method of claim 2, wherein the population of allogeneic T cells is derived from a donor other than the transplant donor.

42. The method of claim 2, which further comprises prior to said administering step a step of generating the population of allogeneic T cells in vitro.

43. The method of claim 42, wherein the step of generating the population of allogeneic T cells in vitro comprises sensitizing allogeneic T cells to CMVpp65.

44. The method of claim 2, wherein the administering is by infusion of the population of allogeneic T cells.

45. The method of claim 2, further comprising, after administering to the human patient the population of allogeneic T cells, administering to the human patient a second population of allogeneic T cells comprising CMV-specific T cells that recognize CMVpp65; wherein the second population of allogeneic T cells is restricted by a different HLA allele shared with at least some, optionally all, of the CMV-infected cells.

46. The method of claim 2, wherein the human patient has failed a previous therapy to treat the CMV retinitis.

47. The method of claim 46, wherein the CMV retinitis is resistant to the previous therapy.

48. The method of claim 47, wherein the previous therapy is treatment with at least one anti-viral agent.

49. The method of claim 46, wherein the previous therapy is treatment with at least one anti-viral agent.

50. The method of claim 49, wherein the at least one anti-viral agent is selected from the group consisting of ganciclovir, foscarnet, valganciclovir, cidofovir, leflunomide, and combinations thereof.

51. The method of claim 2, wherein a CMV in the human patient has at least one mutation in its genome that confers resistance to one or more anti-viral agents.

52. The method of claim 51, wherein the one or more anti-viral agents are selected from the group consisting of ganciclovir, foscarnet, valganciclovir, cidofovir, leflunomide, and combinations thereof.

53. The method of claim 51, wherein the at least one mutation is a mutation in the UL97 gene, a mutation in the UL54 gene, or a first mutation in the UL97 gene and a second mutation in the UL54 gene.

54. The method of claim 51, which further comprises prior to said administering step a step of genotyping a CMV of the human patient.

* * * * *